US008655049B2

(12) United States Patent
Yanai

(10) Patent No.: US 8,655,049 B2
(45) Date of Patent: *Feb. 18, 2014

(54) IDENTIFICATION METHOD OF DATA POINT DISTRIBUTION AREA ON COORDINATE PLANE AND RECORDING MEDIUM

(75) Inventor: Hirokazu Yanai, Osaka (JP)

(73) Assignee: Ricoh Company, Ltd., Tokyo (JP)

( * ) Notice: Subject to any disclaimer, the term of this patent is extended or adjusted under 35 U.S.C. 154(b) by 398 days.

This patent is subject to a terminal disclaimer.

(21) Appl. No.: 13/043,729

(22) Filed: Mar. 9, 2011

(65) Prior Publication Data

US 2011/0229011 A1    Sep. 22, 2011

(30) Foreign Application Priority Data

Mar. 18, 2010   (JP) .................................. 2010-061868

(51) Int. Cl.
*G06K 9/00*    (2006.01)

(52) U.S. Cl.
USPC ............................ 382/141; 382/145; 382/147

(58) Field of Classification Search
USPC ......... 382/141, 144, 145, 146, 147, 148, 149, 382/150, 151
See application file for complete search history.

(56) References Cited

U.S. PATENT DOCUMENTS

| | | | |
|---|---|---|---|
| 5,240,866 A | 8/1993 | Friedman et al. | |
| 5,631,982 A * | 5/1997 | Inselberg et al. | ............. 382/281 |
| 6,996,267 B2 * | 2/2006 | Tabata | ......................... 382/154 |
| 2002/0181756 A1 | 12/2002 | Shibuya et al. | |
| 2004/0064269 A1 | 4/2004 | Shibuya et al. | |
| 2009/0000995 A1 | 1/2009 | Yanai | |
| 2009/0052765 A1 | 2/2009 | Toyoda et al. | |
| 2009/0082979 A1 | 3/2009 | Sato | |
| 2010/0110078 A1 | 5/2010 | Yanai | |

FOREIGN PATENT DOCUMENTS

| | | |
|---|---|---|
| JP | 6-61314 | 3/1994 |
| JP | 10-107102 | 4/1998 |
| JP | 4038356 | 11/2007 |
| JP | 2009-10303 | 1/2009 |
| JP | 2009-71230 | 4/2009 |
| JP | 2009-71271 | 4/2009 |
| JP | 2009-98123 | 5/2009 |
| JP | 4310090 | 5/2009 |
| JP | 2010-27910 | 2/2010 |
| JP | 2010-108236 | 5/2010 |
| JP | 2010-129597 | 6/2010 |
| WO | WO 2010/010907 A1 | 1/2010 |

* cited by examiner

*Primary Examiner* — Brian Le
(74) *Attorney, Agent, or Firm* — Cooper & Dunham LLP

(57) ABSTRACT

A disclosed method of identifying a data point distribution area having data points on a coordinate plane includes dividing a coordinate plane area into plural divided areas using lines; in each divided area, selecting outermost data point data as representative points, and connecting the selected representative points to define a distribution area; comparing the area with a reference area to determine an overlapping area; and determining that the distribution area is a relevant area based on the existence of the overlapping area.

19 Claims, 28 Drawing Sheets

IDENTIFICATION METHOD OF DATA POINT DISTRIBUTION AREA ON COORDINATE PLANE AND RECORDING MEDIUM

CROSS-REFERENCE TO RELATED APPLICATIONS

The present application claims priority under 35 U.S.C §119 based on Japanese Patent Application No. 2010-061868 filed Mar. 18, 2010, the entire contents of which are hereby incorporated herein by reference.

BACKGROUND OF THE INVENTION

1. Field of the Invention

The present invention relates to an identification method of determining whether a data point distribution area is distributed in a specific determination area and a recording medium storing a program causing a computer to execute the identification method.

2. Description of the Related Art

Semiconductor devices (a.k.a chips) are manufactured through various processes. Various defects during the various processes may cause the degradation of the quality and the decrease of the yield rate of the semiconductor devices. In this regard, to improve and stabilize the yield rate, the pattern defect inspection and the particle (contamination) inspection are conducted after a predetermined process to check the existence of the defects.

Further, in each process, after the pattern is formed, the electric characteristic test (wafer test) is performed on each chip on the wafer to detect the defects.

Of the information obtained as a result of inspection or test, there is information indicating defects on a wafer and a distribution of defective chips. In the following, the defects on the wafer or the distribution of defective chips is called "defect distribution".

The defect distribution may be classified into two types: in one type, the defects are substantially uniformly distributed across the wafer without being concentrated on a specific area(s) on the wafer; and in the other type, the defects are un-evenly distributed and may be concentrated on one or more the specific areas on the wafer. The defects in the former type where the defects are evenly distributed may be called random defects. On the other hand, the defects in the latter type where the defects are concentrated on a part of the wafer may be called clustering defects.

The defect distribution in which the detects are concentrated (hereinafter "concentrated defect distribution") is mainly caused by the problems in the manufacturing processes, manufacturing apparatuses and the like. Because of this feature, by investigating the manufacturing processes, the manufacturing apparatuses, and the like, the cause of the lowering of the yield rate may be detected.

As one example of using the information, a status of the defect distribution on a wafer is analyzed first, and based on the analysis, the cause of the defects in the manufacturing processes, manufacturing apparatuses, and the like is estimated (see, for example, Patent Documents 1 and 2).

Patent document 1 describes a method of specifying a cause of defect by classifying the wafer based on a status of the clustered defect distribution and then determining whether the status is similar to a known pattern of the defect distribution.

Patent document 2 describes a method of classifying the categories of the defects based on the distribution status of the defects into repetitive defects, congestion defects, liner defects, ring/lump defects, random defects and the like.

Generally, the position of the chip is expressed using the X axis and the Y axis. To express the information of data group indicating the chip positions on a wafer, those data are expressed on the XY rectangular coordinate plane.

As described above, the concentrated defect distribution in the manufacturing process of manufacturing the semiconductor devices may be caused by the problems in the manufacturing apparatus and the like. Therefore, when the concentrated defect distribution is detected, a defective process may be estimated by collecting the information of lots of the wafers having a similar status of the defect distribution and then investigating the relevant recorded data indicating, for example, which processing apparatus was used and when the process was performed in the manufacturing processes.

In this case, whether the defective distribution is similar to the known pattern of the defect distribution is determined depending on whether the detective distribution exists on a specific area on a wafer (coordinate plane).

In the methods of Patent Documents 1 and 2, the position of the defective distribution is specified by processing data indicating the positions of the defects and defective chips. However, all of the data points of the defective distribution have respective data (e.g., positional information). Namely, under a status where all the data points included in the data point distribution area on the coordinate plane have the respective data, it is determined whether the data point distribution area is distributed on a specified determination area set on the coordinate plane.

Patent Document 1: Japanese Patent Application Publication No. 06-61314
Patent Document 2: Japanese Patent No. 4038356

SUMMARY OF THE INVENTION

According to one aspect of the present invention, while the information amount expressing the data point distribution area on the coordinate plane is decreased, it is determined whether the data point distribution area is distributed on a specified determination area set on the coordinate plane.

According to another aspect of the present invention, there is provided an identification method of identifying a data point distribution area on a coordinate plane. The identification method includes a distribution representative point selection step of dividing an area on the coordinate plane into two or more divided areas by providing and using one dividing straight line or plural dividing straight lines parallel to each other, plural data being expressed as data points on the coordinate plane, the plural data constituting a data group to be determined, each of the plural data including two variables as a pair, the dividing straight line or the plural dividing straight lines crossing the data point distribution area, the data point distribution area being a distribution area of the data points, and selecting, in each of the divided areas, from among the data points in the divided area, an outermost data point in each of two directions as representative points of the data point distribution area, the two directions being parallel to an extending direction of the dividing straight line or plural dividing straight lines; and a determination step of determining whether there is an overlapping area where a distribution representative point area overlaps a determination area, the distribution representative point area being defined by connecting the representative points with lines, the determination area being a specific area set on the coordinate plane, and further determining, when determining that there is the overlapping area, that the data group to be determined is a relevant data group.

BRIEF DESCRIPTION OF THE DRAWINGS

Other objects, features, and advantages of the present invention will become more apparent from the following description when read in conjunction with the accompanying drawings, in which.

DETAILED DESCRIPTION OF THE PREFERRED EMBODIMENTS

First, an embodiment of the present invention is described with reference to result data of pattern defect.

Figure 1:
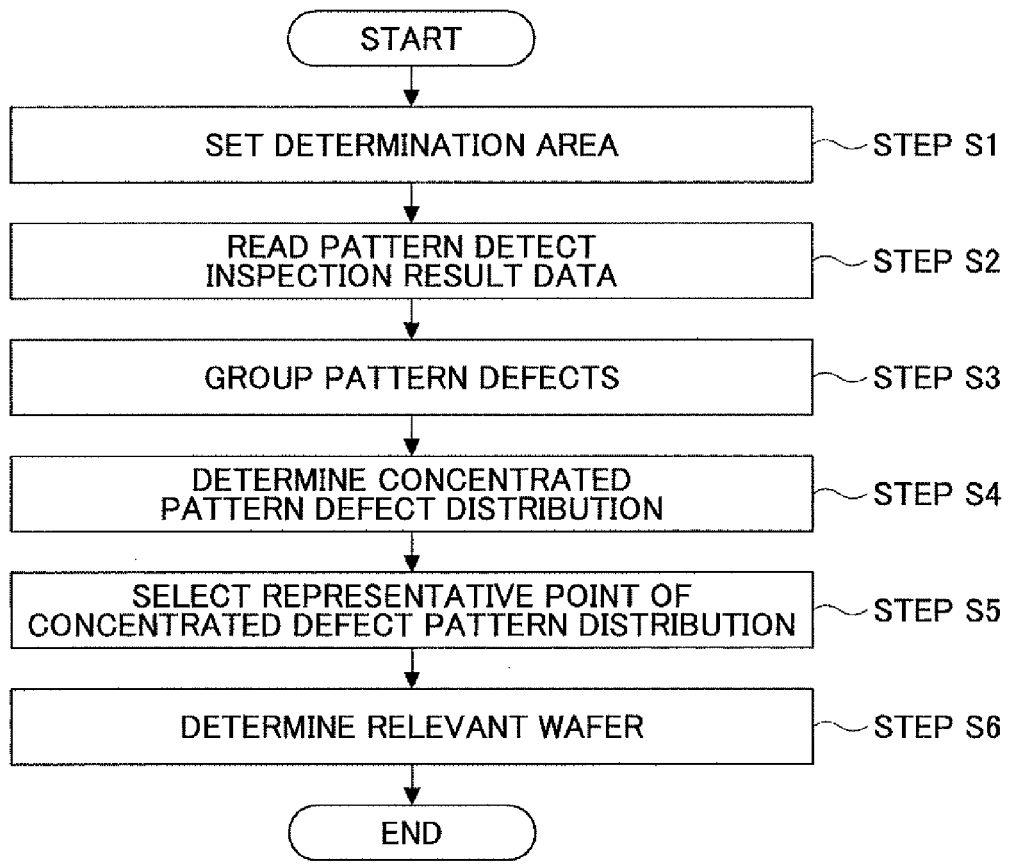
FIG. 1 is a flowchart illustrating a processing procedure of a method according to an embodiment of the present invention.
Figure 2:
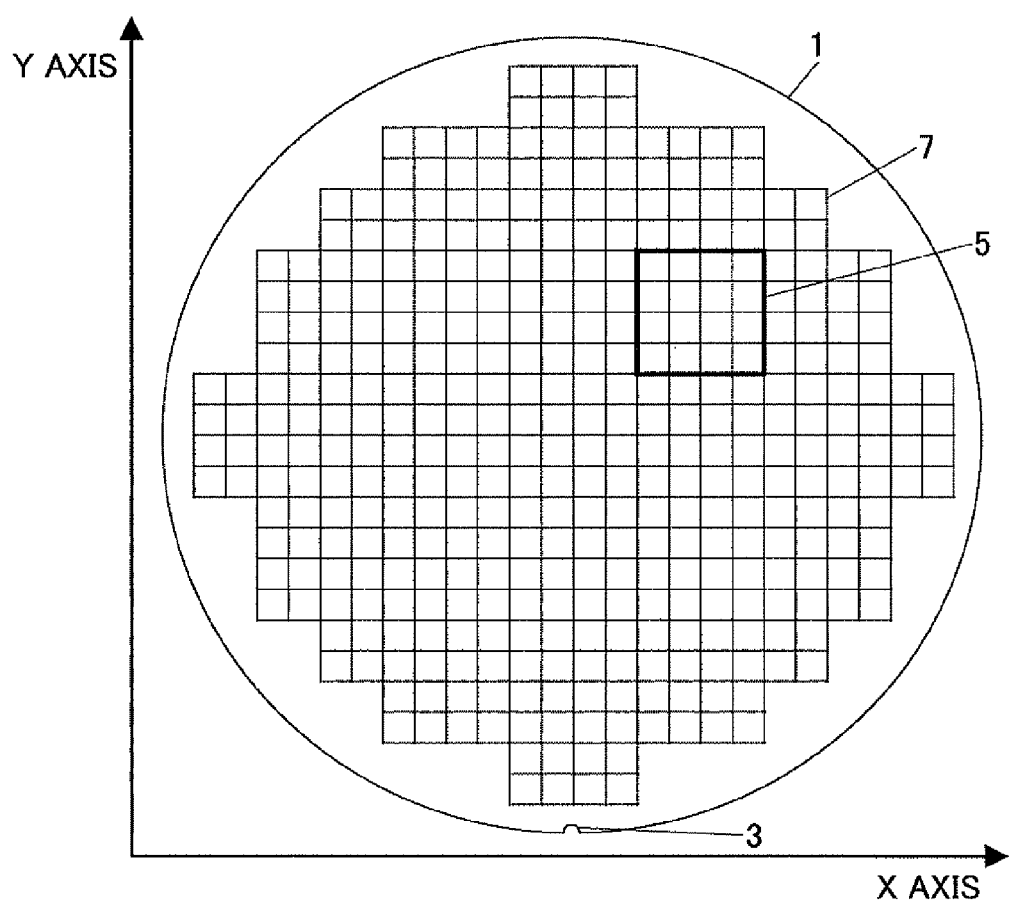
FIG. 2 is a drawing illustrating a determination area set on a wafer.
Figure 3:
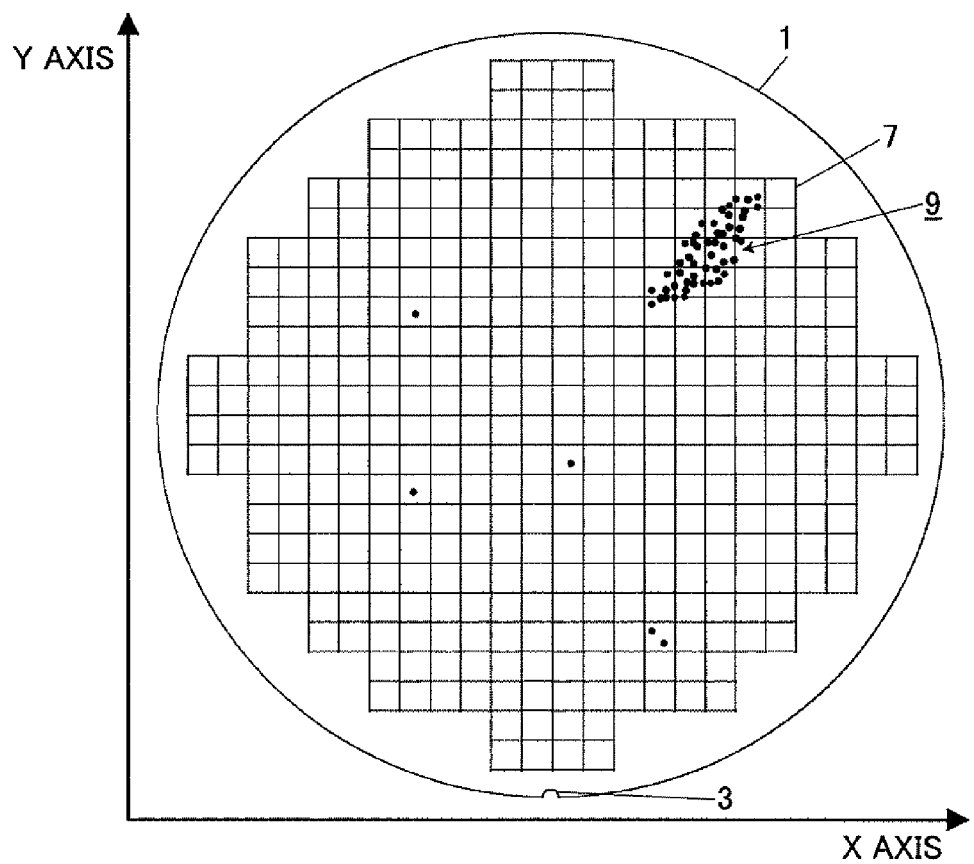
FIG. 3 is a drawing illustrating a concentrated pattern defect distribution on the wafer.
Figure 4:
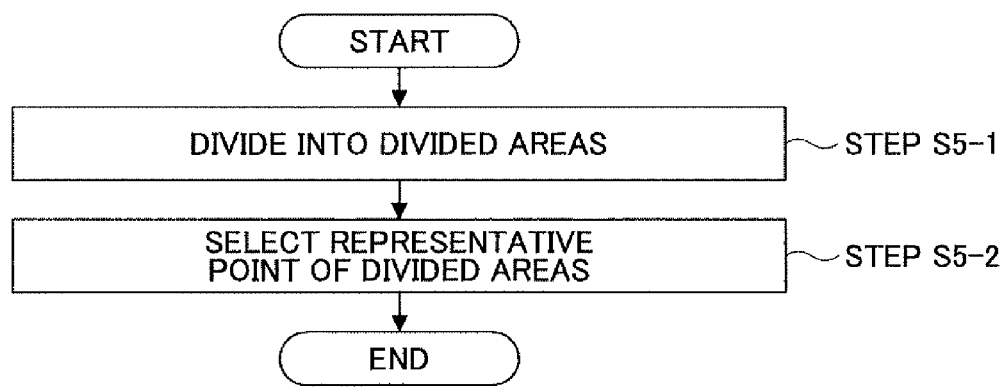
FIG. 4 is a flowchart illustrating a distribution representative point selection step for the concentrated pattern defect distribution.
Figure 5:
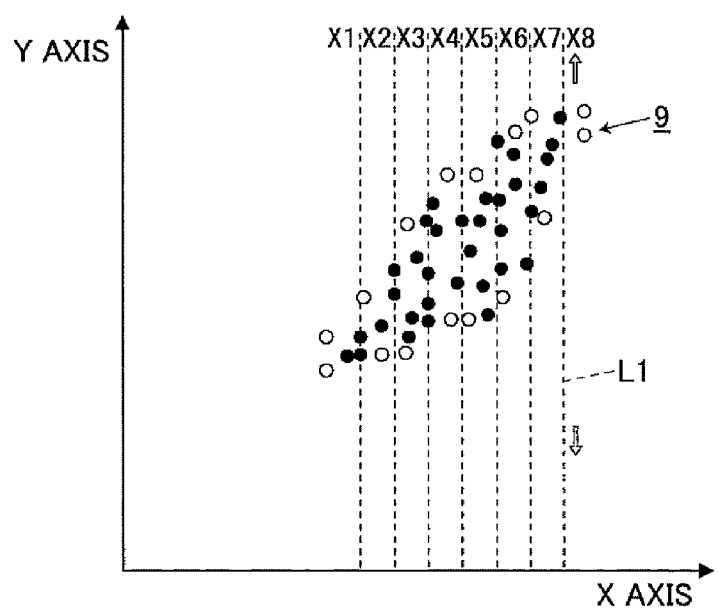
FIG. 5 is an enlarged view of the concentrated pattern defect distribution of FIG. 3, the view including dividing straight lines along the Y axis to divide the area of the concentrated pattern defect distribution into eight (8) areas.
Figure 6:
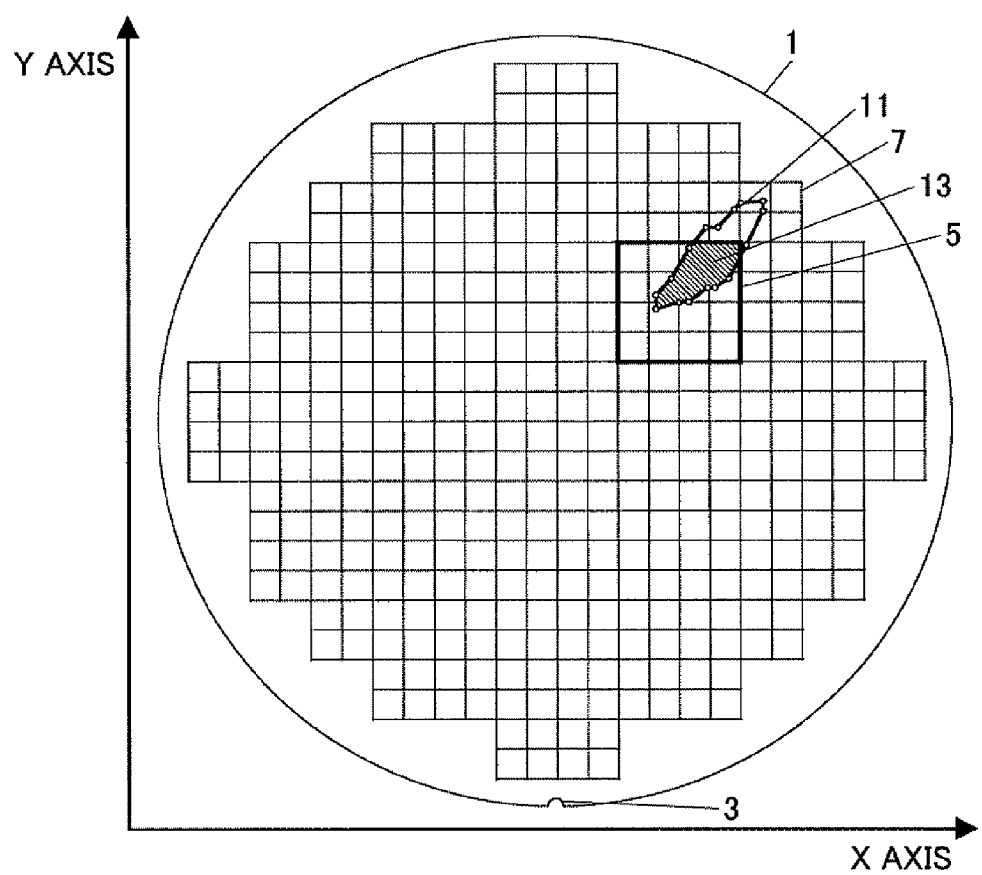
FIG. 6 is a drawing in which the determination area and a concentrated pattern defect distribution representative point area are displayed so as to be overlapped with each other.

FIG. 1 is a flowchart illustrating a method according to an embodiment of the present invention. FIG. 2 illustrates a determination area set on a wafer. FIG. 3 illustrates pattern defect positions on the wafer. FIG. 4 is a flowchart illustrating a distribution representative point selection step of a concentrated pattern defect distribution. FIG. 5 is an enlarged view of a pattern defect group and further illustrates dividing straight lines along the Y axis to divide the area into eight (8) areas. FIG. 6 illustrates the determination area and the concentrated pattern defect representative point area so as to be overlapped with each other on the same coordinate plane. With reference to FIGS. 1 through 6, this embodiment is described. Herein, the Y axis direction refers to the direction parallel to the Y axis, and the X axis direction refers to the direction parallel to the X axis.

Step S1: A determination area 5 is set on the coordinate plane of a pattern defect inspection result. Herein, it is assumed that the determination area 5 is set on a part of upper right-hand side when a wafer 1 is set in a manner such that a notch 3 of the wafer 1 is arranged on the lower side as illustrated in FIG. 2. The notch 3 is a mark on the wafer 1 so that the crystal orientation of the silicon can be recognized. The wafer 1 includes chips 7 arranged in a matrix manner.

Step S2: Next, pattern defect inspection result data associated with target wafer information (i.e., information of the wafer to be determined (inspected)) are read from an inspection apparatus or a database storing the pattern defect inspection result data. The pattern defect inspection result data includes positional coordinate information of pattern defects. FIG. 3 illustrates pattern defect positions on the wafer 1. In FIG. 3, the pattern defects are expressed as dots.

Step S3: Next, the pattern defects are grouped. To that end, for example, mutual distances between the data points representing the pattern defects are obtained. Then, the data points having the mutual distance less than a predetermined threshold value are determined to be included in the same group. However, a method of grouping the data points is not limited to this method, and any other appropriate method may alternatively used.

Step S4: Next, the concentrated pattern defect distribution is selected (determined) from the groups of the pattern defects. To that end, for each of the groups of the pattern defect, it is determined whether the number of the pattern defects is equal to or greater than, for example, five (5). In this case, when determining that the number of the pattern defects is equal to or greater than five (5), the pattern defect group is determined to be the concentrated pattern defect distribution. In this case, the pattern defect group on the upper right-hand side on the wafer of FIG. 3 is determined to be the concentrated pattern defect distribution 9. In this embodiment, the data points included in the concentrated pattern defect distribution 9 are a data group to be determined. However, in this case, all pattern defect data may be treated as the data group to be determined, or only the pattern defect data in a specific area may be treated as the data group to be determined. Further, in this embodiment, the data points included in the concentrated pattern defect distribution 9 are candidates to be selected as the representative points of the data point distribution area.

Step S5: Next, the representative points of the concentrated pattern defect distribution 9 are determined (selected). To that end, plural data points representing the contour (outline) of the distribution area of the concentrated pattern defect distribution 9 are determined (selected) to be the representative points of the concentrated pattern defect distribution 9. With reference to FIGS. 4 and 5, a step of selecting the representative points of the distribution area (hereinafter "distribution representative point selection step") is described.

Step S5-1: As illustrated in FIG. 5, seven dividing straight lines L1 are provided to divide the distribution area of the concentrated pattern defect distribution 9 into, for example, eight (8) divided areas X1 through X8. In this example, the seven (7) dividing straight lines L1 are parallel to the Y axis (one of the coordinate axes). However, the number of the divided areas are not limited to eight (8). Any appropriate number greater than one (1) may be selected as the number of the divided areas. Further, the dividing straight lines may be parallel to the X axis.

Step S5-2: Next, the representative points for each of the divided areas X1 through X8 are determined. To that end, in each of the divided areas X1 through X8, the data points disposed at the outermost positions along the two extending directions of the dividing straight lines L1 are selected as the representative points. In this case, in each of the divided areas X1 through X8, the data point having the maximum value in the Y axis direction is selected as the maximum value side representative point, and the data point having the minimum value in the Y axis direction is selected as the minimum value side representative point. In FIG. 5, the data points selected as the representative points are displayed as white circles, and the data points other than the representative points are displayed as black circles.

In this embodiment, the "two extending directions of the dividing straight lines" refer to the directions expressed using the respective white arrows. In this embodiment, one of the two directions is the same as the plus direction of the Y axis coordinate, and the rest of the two direction is the same as the minus direction of the Y axis coordinate. Further, in an identification method according to an embodiment of the present invention, the data points disposed at the outermost positions along the two extending directions of the dividing straight lines L1 refer to the data point having the maximum value in the Y axis coordinate and the data point having the minimum value in the Y axis coordinate in the respective divided areas.

It is thought that there are various methods of determining the representative points in each of the divided areas.

For example, first, based on the X axis coordinate value of a first data point, the divided area of the first data point (i.e., the divided area to which the first point belongs) is determined. The coordinate of the first data point is memorized (stored) as a maximum value side representative point candidate in the divided area of the data point. Next, the divided area of the next data point is determined. When there is already the maximum value side representative point candidate in the divided area of the data point, a comparison is made between the Y axis coordinate value of the data point and the Y axis coordinate value of the maximum value side representative point candidate. As a result of the comparison, when determining that the Y axis coordinate value of the data point is greater than the Y axis coordinate value of the maximum value side representative point candidate, the coordinate of the data point is stored as a new maximum value side representative point candidate in the divided area. On the other hand, when determining that the Y axis coordinate value of the data point is less than the Y axis coordinate value of the maximum value side representative point candidate, the information of the maximum value side representative point candidate is unchanged. Further, when determining that the Y axis coordinate value of the data point is equal to the Y axis coordinate value of the maximum value side representative point candidate, the coordinate of the data point is stored as a new maximum value side representative point candidate in the divided area and the information of the maximum value side representative point candidate is also maintained.

On the other hand, when there is no maximum value side representative point candidate in the divided area of the data point, the data point is stored as the maximum value side representative point candidate in the divided area. After that, the above procedure is repeated for all of the data points, so that the maximum value side representative point candidates of the respective divided areas are determined. After the above process is completed for all the data points, the representative point candidates in the respective divided areas are stored as the maximum value side representative points. The minimum value side representative points in the respective divided areas are also selected in the same manner. Namely, to select the minimum value side representative points, the comparison is made to select the data point having a lesser Y axis coordinate value in the above processes.

However, the method of determining the representative points is not limited to the method described above. For example, the first data point may be set as the maximum value side representative point candidate or the minimum value side representative point candidate of the divided area of the data point. Then, for the next point, based on the comparison in the Y axis coordinate value between the next point and the data point of the representative point candidate, one may be set as the maximum value side representative point candidate and the other may be set as the minimum value side representative point candidate of the divided area. Next, for the next data point, the comparisons in the Y axis coordinate values are made among of the next data, the maximum value side representative point candidate, and the minimum value side representative point candidate. Based on the comparison results, the maximum value side representative point candidate and the minimum value side representative point candidate may be updated.

Otherwise, the representative points may be determined by grouping the data points based on the divided areas, comparing the Y axis coordinate values of the data points for each divided area, and determining the representative points based on the comparison results.

Further, when there is a divided area in which no data point is included, the subsequent process may be performed assuming that the divided area has no representative point.

Further, in the above description with reference to FIG. 3, a case is described where the number of the concentrated pattern defect distributions 9 is one (1). However, in step S4, when determining that plural concentrated pattern defect distributions 9 are detected for the pattern defect inspection data of the wafer information, the distribution representative point selection step of step S5 is performed on each of the plural concentrated pattern defect distributions 9.

Referring back to FIG. 1, the method in the flowchart of FIG. 1 is further described.

Step S6: It is determined whether there is an overlapping area 13 where a concentrated pattern defect distribution representative point area 11 overlaps the determination area 5, the concentrated pattern defect distribution representative point area 11 being formed by sequentially connecting the representative points of the concentrated pattern defect distribution 9 using lines. In this case, the concentrated pattern defect distribution representative point area 11 is defined by sequentially connecting sixteen (16) representative points with lines in a manner such that the lines are not crossed over each other. For example, such a concentrated pattern defect distribution representative point area 11 may be defined by connecting from the representative point as the start point to the next representing point of the adjacent area with a line and connecting in the same manner in the clockwise or counterclockwise direction. In FIG. 6, a case is described that the lines between the representative points are straight lines. However, the present invention is not limited to this configuration. For example, by using the "DrawClosedCurve" method of Visual Basic (trade mark of Microsoft Corp.) or the like, the representative points of the concentrated pattern defect distribution representative point area 11 may be connected with smooth curves passing through the representative points. This alternative connecting method may also be applied to the other embodiments described below.

As illustrated in FIG. 6, the concentrated pattern defect distribution representative point area 11 overlaps the determination area 5 forming the overlapping area 13. Therefore, it is determined that the concentrated pattern defect distribution 9 is determined to be the data group to be obtained (hereinafter may be referred to as a "relevant data group"). Further, the wafer information corresponding to the pattern defect inspection result data including the concentrated pattern defect distribution 9 is determined to be the wafer information having the pattern defect distribution to be obtained.

Further, in a case where, in step S4, it is determined that there are plural concentrated pattern defect distributions in one wafer information, and when, in step S5, the selection process of the representative points are selected for each of the concentrated pattern defect distributions, the distribution representative point area is defined for each of the concentrated pattern defect distributions, and it is determined whether there is the overlapped area where the distribution representative point area overlaps the determination area for each of the distribution representative point areas.

In this embodiment, the concentrated pattern defect distribution representative point area 11 is expressed by using sixteen (16) representative points. Because of this feature, the information amount expressing the concentrated pattern defect distribution representative point area 11 is less than the information amount expressing the concentrated pattern defect distribution 9. Namely, in this embodiment, it can be determined whether the concentrated pattern defect distribution 9 is distributed in the specific determination area 5 while the information amount expressing the concentrated pattern defect distribution 9 is reduced by replacing the concentrated pattern defect distribution 9 with the concentrated pattern defect distribution representative point area 11.

In the embodiment described with reference to the flowchart of FIG. 1, whenever the determination step S6 is executed, the pattern defect data point group is formed (step S3), the concentrated pattern defect distribution is determined (step S4), and the representative points of the concentrated pattern defect distribution are selected (step S5).

However, when those processes are performed on the stored data and the processes are performed using the same references, it may be more reasonable to perform the representative point selection process on the data points (data group to be determined) when the data are collected, the data points being included in the concentrated pattern defect distribution, so that the representative point information is associated with the wafer information (identification information of data group to be determined) and stored in the database as the data. The embodiment is described with reference to FIG. 7.

Figure 7:
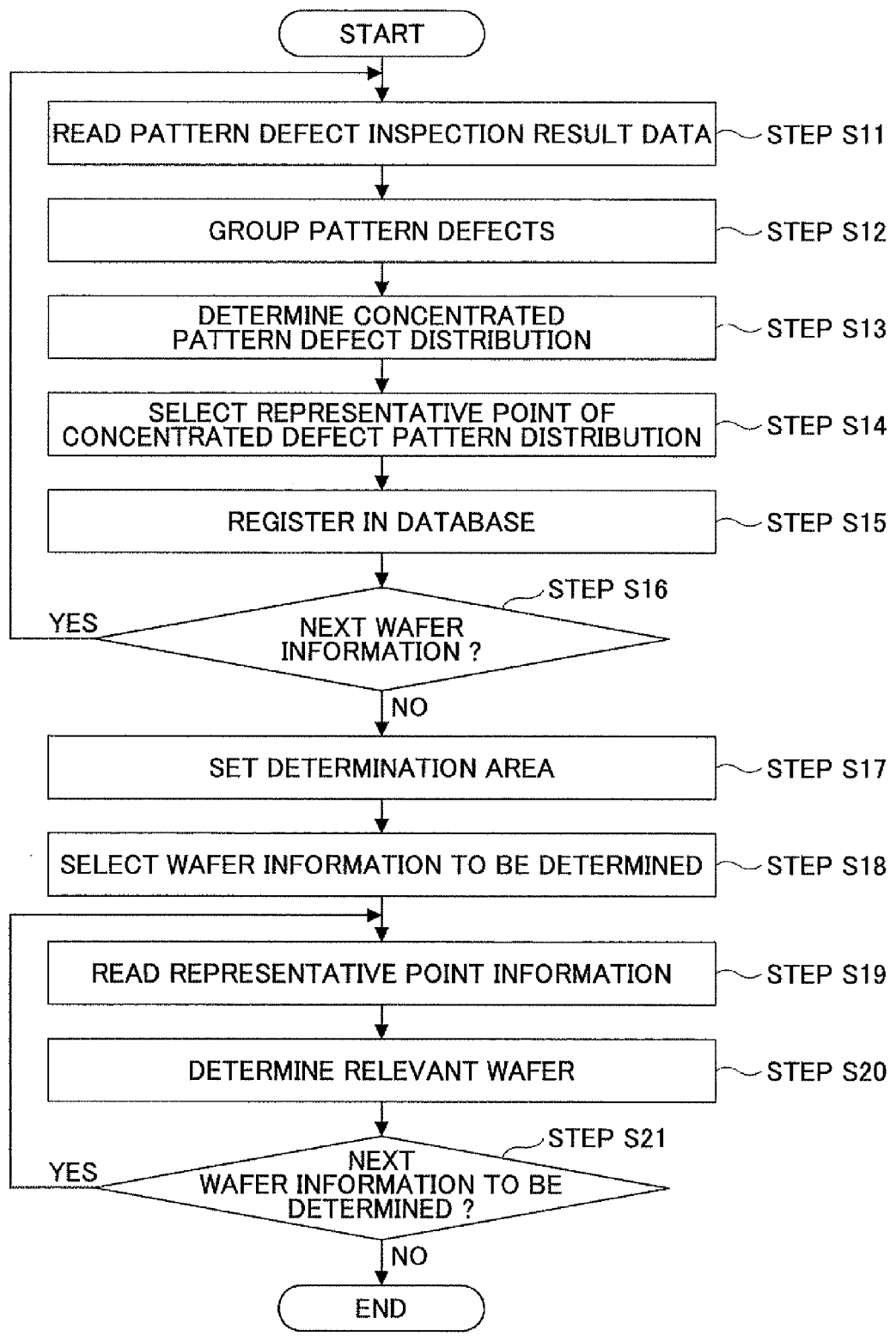
FIG. 7 is a flowchart illustrating a processing procedure of a method according to another embodiment of the present invention.

FIG. 7 is a flowchart illustrating a method according to another embodiment of the present invention. In this embodiment, the steps already described with reference to the flowchart of FIG. 1 may be described in a simple manner.

Steps S11 through S14: Similar to steps S2 through S5 of FIG. 1, the pattern defect inspection result data associated with the wafer information is read (step S11); the pattern defects are grouped (step S12); it is determined that the pattern defect is the concentrated pattern defect distribution (step S13); and the representative points of the concentrated pattern defect distribution are selected, the representative points representing the contour of the concentrated pattern defect distribution (step S14).

Step S15: the representative points information acquired in step S14 is associated with the wafer information and registered in the database. In this case, the distribution range of the concentrated pattern defect distribution and characteristic information may also be associated with the wafer information and registered in the database, the characteristic information including at least one of an area (size), a roundness rate, and a data point distribution density of the distribution representative point area defined by sequentially connecting the representative points with lines in a manner such that the lines are not crossed over each other. Further, there are various information to be associated with the wafer information, the various information including a lot number, a manufacturing method, a product type name, a process name, an inspection completion date, and the like for identifying the wafer. Further, when the wafer test is completed, as the wafer test result information, the information such as the determination test result (PASS or FAIL) of the chips, the test category corresponding to the FAIL test result, may also be associated with the wafer information.

Step S16: It is determined whether next wafer information exists. When determining that the next wafer information exists (YES in step 16), the process goes back to step S11 and the processes of steps S11 through S15 are performed on the next wafer information. When determining that there is no wafer information (NO in step 16), the process goes to step S17.

Step S17: The determination area is set on the coordinate plane.

Step S18: From among the wafer information registered in the database, the wafer information to be determined is selected as the wafer information to be determined. For example, the wafer information to be determined having the representative points of the concentrated pattern defect distribution located in the determination area set in step S17 is selected. Otherwise, if the characteristic information is associated and registered with the wafer information in step S15, the wafer information to be determined may be selected based on the characteristic information. Otherwise, the wafer information to be determined may be selected based on the information indicating the lot number, the product type name, the inspection execution date or the like.

Step S19: The representative point information of the wafer information selected in step S18 is read.

Step S20: Similar to step S6 of FIG. 1, it is determined whether there is the overlapping area where the concentrated pattern defect distribution area overlaps the determination area. When determining that there is the overlapping area, the concentrated pattern defect distribution area is determined to be the wafer information having the pattern defect inspection result data including the pattern defect distribution to be obtained.

Step S21: It is determined whether any of the wafer information to be determined selected in step S18 is remaining. When determining that any of the wafer information to be determined selected in step S18 is remaining (YES in step S21), the process goes back to step S19 to perform the processes of steps S19 and S20 on the next wafer information to be determined. When determining that none of the wafer information to be determined selected in step S18 is remaining (NO in step S21), the process ends.

In step S15, the representative points information may be associated with the wafer information to be determined and registered in database. By doing this, it may become possible to skip the distribution representative point selection step of steps S11 through S14 by reading the representative point information from the database to perform the wafer determination (in step S20). As a result, the processing time may be reduced.

Further, the information amount of the representative points of the concentrated pattern defect distribution is less than the information amount of all defect data points included in the concentrated pattern defect distribution 9. Therefore, it may become possible to reduce the reading time and the processing time.

In the above embodiments, in steps S6 and S20 where the wafer information is determined, the determination may be made depending on whether the area of the concentrated pattern defect distribution representative point area 11 is equal to or greater than a predetermined defect distribution representative point area threshold value. In this case, in steps S6 and S20, when determining that the area of the concentrated pattern defect distribution representative point area 11 is less than a predetermined defect distribution representative point area threshold value, it may be determined that the concentrated pattern defect distribution representative point area 11 is not the wafer information to be determined. By doing this, it may become possible to remove the wafer information having the concentrated pattern defect distribution representative point area 11 having the size less than the size of the concentrated pattern defect distribution representative point area 11 of the wafer information to be obtained. Therefore, it may become possible to improve the determination accuracy of the wafer information to be obtained.

This determination process of the area of the distribution representative point area may be performed before or after the determination process of determining the existence of the overlapping area. When the determination process of the area of the distribution representative point area is performed before the determination process of determining the existence of the overlapping area, it may become possible not to perform the determination process of determining the existence of the overlapping area for the distribution representative point area that has a small area and that has to be removed.

Further, in step 6 and 20 where the wafer information is determined, it may be further determined whether the overlapping area 13 is equal to or greater than a predetermined overlapping area threshold value. In steps 6 and 20, when determining that the overlapping area 13 is equal to or greater than the predetermined overlapping area threshold value, it may be determined that the concentrated pattern defect distribution representative point area 11 is the wafer information to be determined. By doing this, it may become possible to improve the determination accuracy of the wafer information.

Further, in step 6 and 20 where the wafer information is determined, it may be further determined whether a ratio of the area of the determination area 5 to the area of the overlapping area 13 is equal to or greater than a predetermined first ratio threshold value. In steps 6 and 20, when determining that the ratio is equal to or greater than the first ratio threshold value, it may be determined that the concentrated pattern defect distribution representative point area 11 is the wafer information to be determined. By doing this, it may become possible to improve the determination accuracy of the wafer information.

Figure 8:
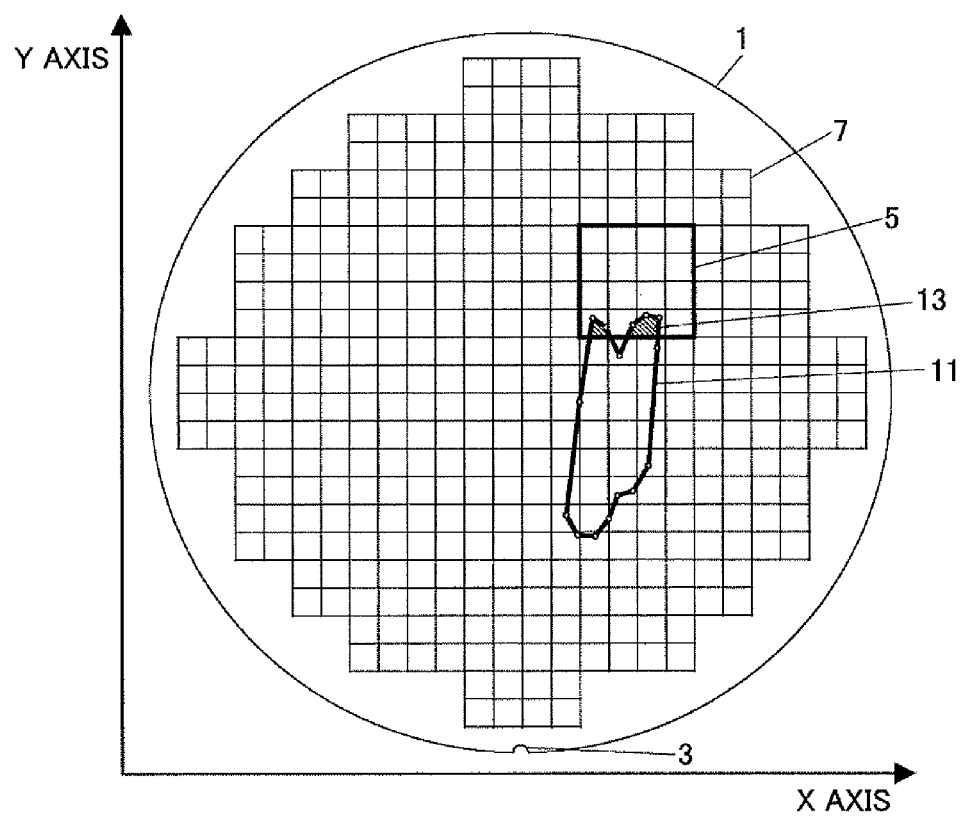
FIG. 8 is a drawing illustrating another example of the positional relationship between the determination area and the concentrated pattern defect distribution.

For example, as illustrated in FIG. 8, the determination area 5 overlaps the concentrated pattern defect distribution representative point area 11. However, when the ratio of the area of the determination area 5 to the area of the overlapping area 13 is less than, for example, 50%, it may be determined that the concentrated pattern defect distribution representative point area 11 is not the wafer information to be determined. By doing this, it may become possible to improve the determination accuracy of the wafer information.

Further, the overlapping area 13 may include plural areas separated from each other.

Further, in steps 6 and 20 where the wafer information is determined, it may be further determined whether a ratio of the area of the overlapping area 13 to the area of the concentrated pattern defect distribution representative point area 11 is equal to or greater than a predetermined second ratio threshold value. In steps 6 and 20, when determining that the ratio is equal to or greater than the second ratio threshold value, it may be determined that the concentrated pattern defect distribution representative point area 11 is the wafer information to be determined.

Figure 9:
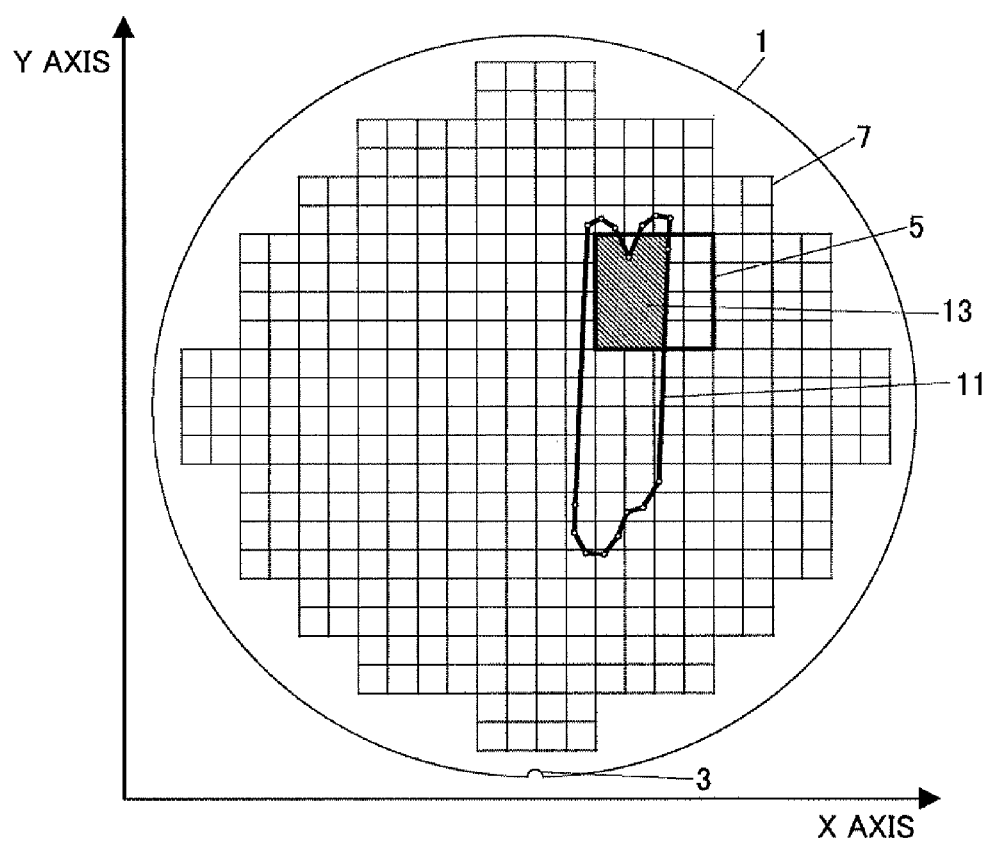
FIG. 9 is a drawing illustrating still another example of the positional relationship between the determination area and the concentrated pattern defect distribution.

For example, as illustrated in FIG. 9, the determination area 5 overlaps the concentrated pattern defect distribution representative point area 11. However, when the ratio of the area of the overlapping area 13 to the area of the concentrated pattern defect distribution representative point area 11 is less than, for example, 50%, it may be determined that the concentrated pattern defect distribution representative point area 11 is not the wafer information to be determined. By doing this, it may become possible to improve the determination accuracy of the wafer information.

Further, in FIG. 8, if the ratio of the area of the overlapping area 13 to the area of the concentrated pattern defect distribution representative point area 11 is less than, for example, 50%, it may be determined that the concentrated pattern defect distribution representative point area 11 is not the wafer information to be determined.

Further, in step 18 of FIG. 7, from among the wafer information to be determined registered in the database, when the wafer information that is to be determined is selected, it may become possible to reduce the processing time when compared with a case where all the wafer information to be determined registered in the database are read. However, the present invention is not limited to this configuration. Namely, all the wafer information to be determined registered in the database may be read.

When the wafer information to be determined is selected, the wafer information to be determined having the representative point of the concentrated pattern defect distribution located in the determination area set in step S17, the wafer information to be determined having a relationship between the determination area 5 and the representative points (white circles) as illustrated in FIG. 6 may be selected.

Figure 10:
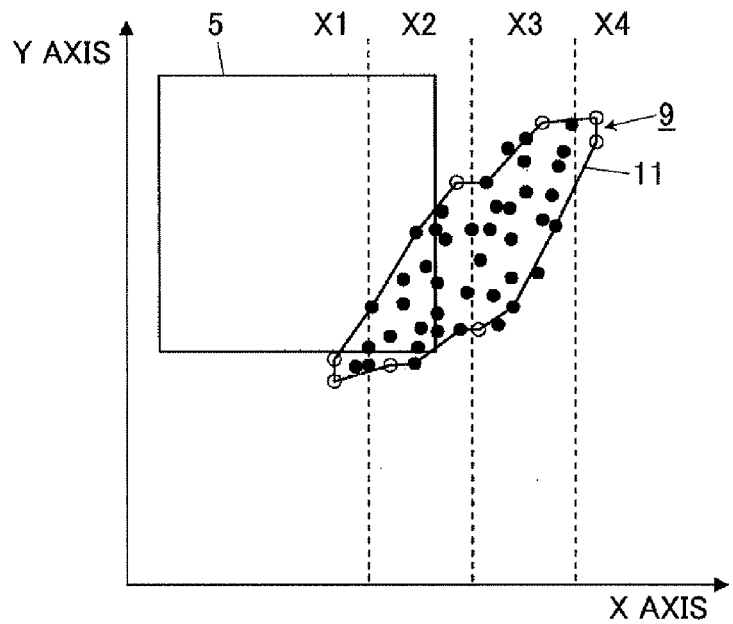
FIG. 10 is a drawing illustrating still another example of the positional relationship between the determination area and the concentrated pattern defect distribution.

However, depending on the disposed position of the determination area 5, for example, as illustrated in FIG. 10, there may be a case where the pattern defect data points (black circles) are disposed in the determination area 5, but none of the representative points (while circles) are disposed in the determination area 5. In the case of the positional relationship between the determination area 5 and the representative points as illustrated in FIG. 10, the wafer information to be determined having the representative points may not be selected in step S18. FIG. 10 illustrates where the area of the coordinate plane is divided into four (4) areas X1 through X4, and the representative points are selected for each of the four (4) areas.

If this is not desirable, in step S15, it may be possible to associate and register the characteristic information including the distribution range of the concentrated defect distribution and at least one of the area of the distributed representative area, the roundness rate, and the data point distribution density with the wafer information to be determined. Further, in step S18, the wafer information to be determined may be selected based on the characteristic information. Specific examples of the characteristic information are described below.

For example, the wafer information to be determined is associated with the distribution range of the concentrated defect distribution.

Figure 11:
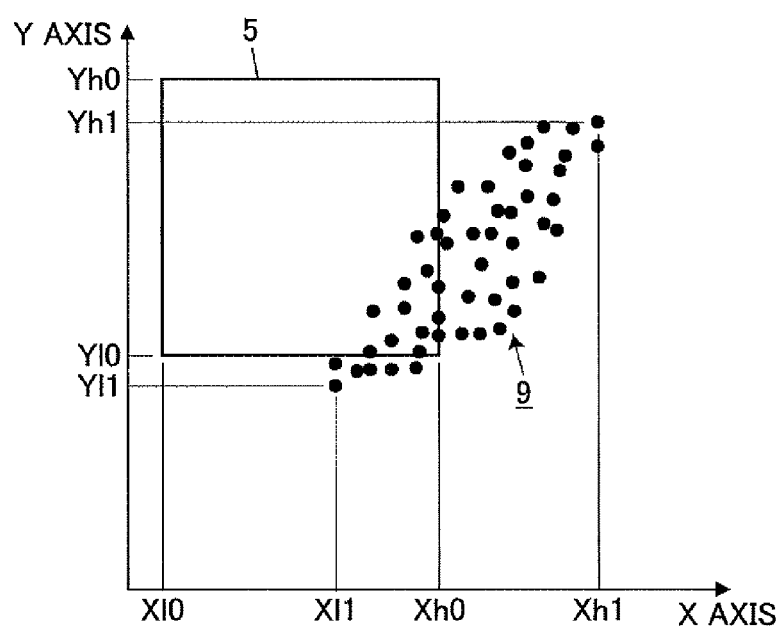
FIG. 11 is a drawing illustrating an example of a distribution range display of the concentrated pattern defect distribution.

FIG. 11 illustrates one example of the distribution range of the concentrated defect distribution. From among the XY coordinate values of all the data points included in the concentrated pattern defect distribution, the information expressing the distribution range of the concentrated pattern defect distribution 9 is expressed by using the four values: the maximum value Xh1 and the minimum value Xl1 of the X axis and the maximum value Yh1 and the minimum value Yl1 of the Y axis. On the other hand, the range of the determination area 5 is expressed by the four values: the maximum value Xh0 and the minimum value Xl0 of the X axis and the maximum value Yh0 and the minimum value Yl0 of the Y axis.

In this case, the search conditions for making a short list of (narrow down, reducing the number of candidates (options)) the wafer information to be determined are: Xh1>Xl0, Xl1<Xho, Yh1>Yl0, and Yl1<Yho.

By setting the conditions in this way, it may become possible to select wafer information having the concentrated pattern defect distribution 9 illustrated in FIG. 11.

In this case, the four (4) values, that is the maximum value Xh1 and the minimum value Xl1 of the X axis and the maximum value Yh1 and the minimum value Yl1 of the Y axis, are obtained by using all the data points included in the concentrated pattern defect distribution 9. However, alternatively, those maximum and minimum values may be obtained using only the representative points as the information expressing the distribution range of the concentrated pattern defect distribution 9.

Figure 12:
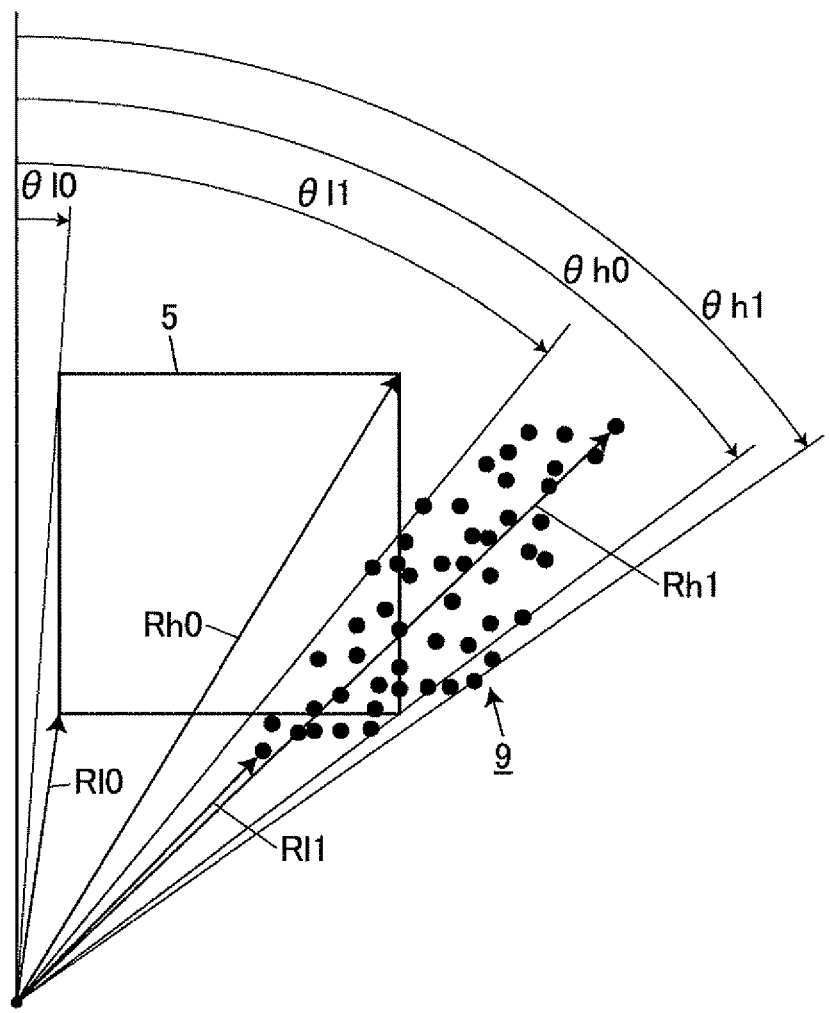
FIG. 12 is a drawing illustrating another example of a distribution range display of the concentrated pattern defect distribution.

FIG. 12 illustrates another example of the distribution range of the concentrated pattern defect distribution 9.

In FIG. 11, the XY coordinate system is used. However, the polar coordinate system may alternatively be used to express the distribution range of the concentrated pattern defect distribution 9.

When the polar coordinate system is used, from among the "R" values and "θ" values of all the data points included in the concentrated pattern defect distribution 9, the information expressing the distribution range of the concentrated pattern defect distribution 9 is expressed by the four values: the maximum value Rh1 and the minimum value Rl1 of the R values and the maximum value θh1 and the minimum value θl1 of the θ values. On the other hand, the range of the determination area 5 is expressed by the four values: the maximum value Rh0 and the minimum value Rl0 of the R values and the maximum value θh0 and the minimum value θl0 of the θ values.

In this case, the search conditions for making a short list of (narrow down) the wafer information to be determined are: Rh1>Rl0, Rl1<Rho, θh1>θl0, and θl1<θho.

By setting the conditions in this way, it may become possible to select wafer information having the concentrated pattern defect distribution 9 illustrated in FIG. 12.

In this case, the four values, that is the maximum value Rh1 and the minimum value Rl1 of the R values and the maximum value θh1 and the minimum value θl1 of the θ values, are obtained by using all the data points included in the concentrated pattern defect distribution 9. However, alternatively, those maximum and minimum values may be obtained using only the representative points as the information expressing the distribution range of the concentrated pattern defect distribution 9.

Further, the area of the concentrated pattern defect distribution representative point area 11 is one of the information expressing the feature of the concentrated pattern defect distribution 9. Therefore, by using the representative points selected in step S14, the area of the concentrated pattern defect distribution representative point area 11 is obtained. Then, in step S15, the area information is associated with the wafer information and registered in the database. Then, in step S18, the wafer information to be determined is selected based on the area of the concentrated pattern defect distribution representative point area 11. By doing in this way, in step S20 where the wafer information is determined, it may become possible to omit the determination process that the concentrated pattern defect distribution representative point area 11 having an area less than a threshold value is not the wafer information to be determined.

Further, the information expressing the feature of the shape of the concentrated pattern defect distribution representative point area 11 may be obtained and registered, so that the information is used for selecting the wafer information to be determined. For example, as a value expressing to what extent the shape of the concentrated pattern defect distribution representative point area 11 is similar to a circle, a value obtained by dividing the area of the concentrated pattern defect distribution representative point area 11 by the area of a circle having a circumference equal to a line length surrounding the concentrated pattern defect distribution representative point area 11 is obtained, and the value (hereinafter "roundness rate") is associated with the wafer information and registered in the database.

In this case, when line length surrounding the concentrated pattern defect distribution representative point area 11 is given as "L", the radius "r" of a circle having the circumference equal to "L" is given as "$L/2\pi$". Further, the area of the circle having the circumference equal to "L" is given as "$\pi r^2 = \pi(L/2\pi)^2 = L^2/4\pi$". When assuming that the area of the concentrated pattern defect distribution representative point area 11 is given as "S", the "roundness rate" is expressed as $S/(L^2/4\pi) = 4\pi S/L^2$.

When the roundness rate approaches 1, the shape approaches a circle, and when the roundness rate approaches 0, the shape approaches a line. Therefore, by using this feature, the "roundness rate" may be used when the wafer information to be determined in the distribution identification target wafer selection step on as needed basis.

Further, the number of pattern defect data points in the concentrated pattern defect distribution representative point area 11, that is the data point distribution density may be one of the information expressing the feature of the concentrated pattern defect distribution.

Figure 13:
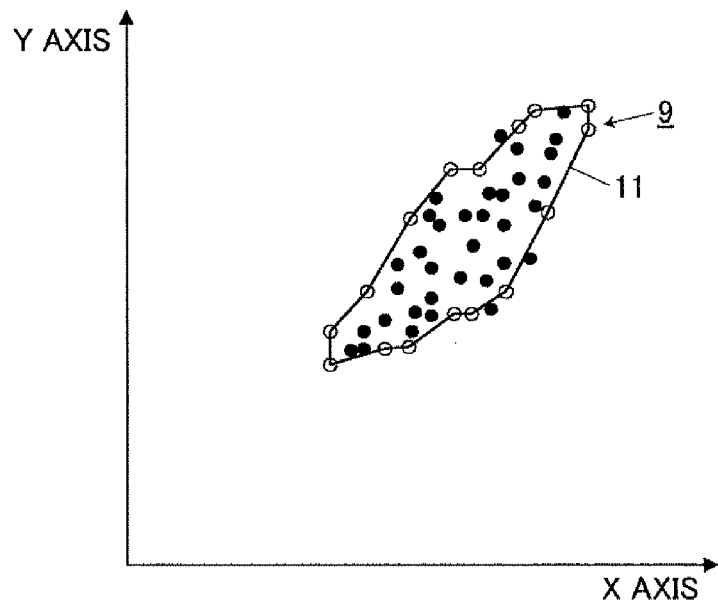
FIG. 13 is a drawing illustrating an example of a data point distribution density in the concentrated pattern defect distribution.
Figure 14:
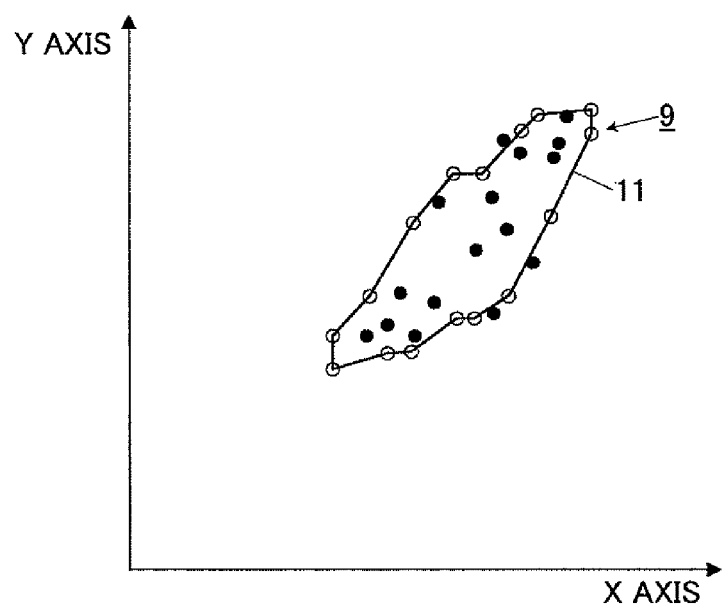
FIG. 14 is a drawing illustrating another example of a data point distribution density in the concentrated pattern defect distribution.

When the concentrated pattern defect distribution representative point area 11 of the concentrated pattern defect distribution 9 in FIG. 13 is compared with the concentrated pattern defect distribution representative point area 11 of the concentrated pattern defect distribution 9 in FIG. 14, the sizes of the concentrated pattern defect distribution representative point areas 11 are the same as each other; however, the numbers of the pattern defect data points differs from each other. Namely, the density of the pattern defect data points in FIG. 13 is higher than the density of the pattern defect data points in FIG. 14. Therefore, the data point distribution density of the data point distribution area of the concentrated pattern defect distribution representative point areas 11 may be obtained in advance, associated with the wafer information, and registered in the database. By doing this, it may become possible to exclude (remove) the concentrated pattern defect distribution 9 having a lower data point distribution density of the data point distribution area of the concentrated pattern defect distribution 9 as illustrated in FIG. 14 and selecting only the concentrated pattern defect distribution 9 having a higher data point distribution density of the data point distribution area of the concentrated pattern defect distribution 9 as illustrated in FIG. 13, so that this feature can be utilized in selecting the wafer information to be determined.

In the above embodiment, the data points indicating the pattern defect position are used. However, by using the data points indicating the particle positions (of foreign matters) based on the particle (contamination) inspection result, the processes similar to the processes in the above embodiment may be performed.

Further, the chip positions corresponding to data point positions indicating the pattern defect positions and particle positions may be regarded as the positions of defective chips. Then, by using the data indicating the defective chip positions, the processes similar to the processes in the above embodiment may be performed. However, there may be no concept of chips in the particle (contamination) inspection result data for a mirror surface wafer. In this case, "virtual" chips may be set on the wafer.

Figure 15:
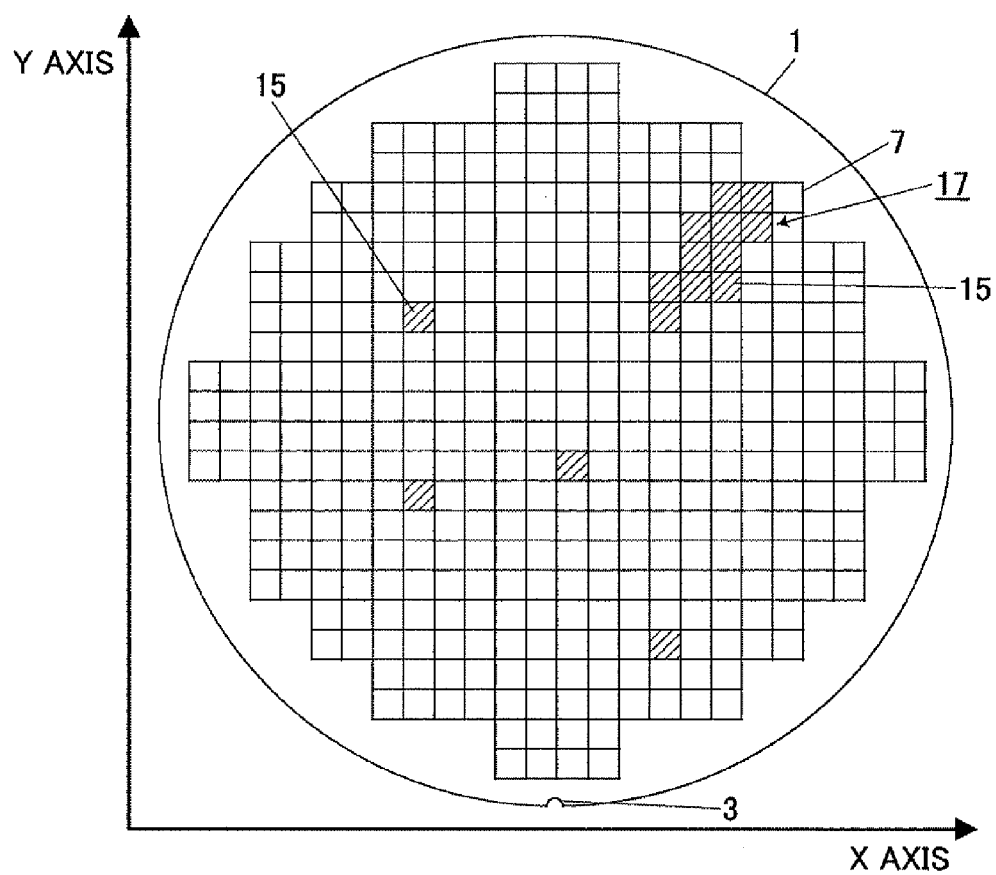
FIG. 15 is a drawing in which the pattern defect positions in FIG. 3 are replaced by defective chips.

For example, FIG. 15 illustrates a case where the pattern defect positions on the wafer of FIG. 3 are replaced by the detective chip positions. In FIG. 15, the defective chips are denoted by the reference numeral 15.

Similar to step S3 described with reference to FIG. 1, the defective chips 15 are grouped in a manner such that the defective chips 15 having the mutual distance less than a predetermined threshold value are determined to be included in the same group. However, a method of grouping the defective chips 15 is not limited to this method, and any other appropriate method may be alternatively used. For example, the defective chips 15 may be grouped based on a method disclosed in Japanese Patent Application Publication No. 2009-10303.

Similar to step S4 described with reference to FIG. 1, for each of the groups of the defective chips 15, it is determined whether the group is the concentrated pattern distribution when the number of the defective chips 15 is five (5) or more. In the case of FIG. 15, the defective chip group 17 is determined to be the concentrated defect distribution.

Figure 16:
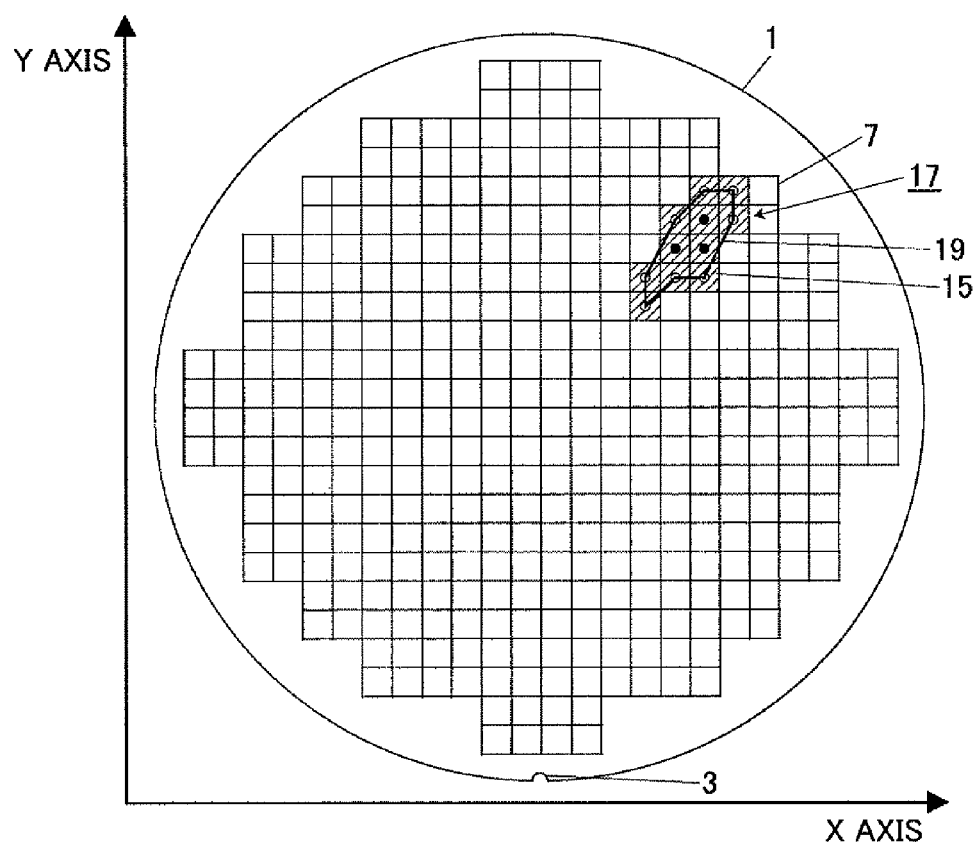
FIG. 16 is a drawing illustrating representative points of a concentrated defect distribution and a representative point distribution area.

Chip positional information refers to the information indicating the positions of the chips 7 on the wafer 1. Therefore, for example, the chip positional information may be replaced by the positional information expressing the center points of the chips 7. By using the positional information expressing the center points of the defective chips 15, for example, chip area border lines extending long the Y axis are used as the dividing straight lines, so that the processes similar to the processes of step S5 described with reference to FIG. 1 and steps S5-1 and S5-2 described with reference to FIG. 4 are performed. As a result, as illustrated in FIG. 16, the representative points (white circles) of the concentrated defect distribution 17 are obtained. In FIG. 16, the black circles and the white circles denote the center points of the defective chips 15 of the concentrated defect distribution 17. FIG. 16 further illustrates a concentrated defect distribution representative point area 19 that is formed by sequentially connecting the representative points of the concentrated defect distribution 17 with lines.

After that, similar to step S6 described with reference to FIG. 1, it is determined whether the concentrated defect distribution representative point area 19 is the wafer information to be determined based on whether there is the overlapping area where the concentrated defect distribution representative point area 19 overlaps the determination area.

In FIG. 15, as described above, the chip positional information is replaced by the positional information expressing the center points of the chips 7. On the other hand, the wafer test result data include chip positional information and the test results (PASS or FAIL) of the chips. Therefore, the processes similar to the processes described with reference to FIGS. 15 and 16 may also be performed on the wafer test result data.

Figure 17:
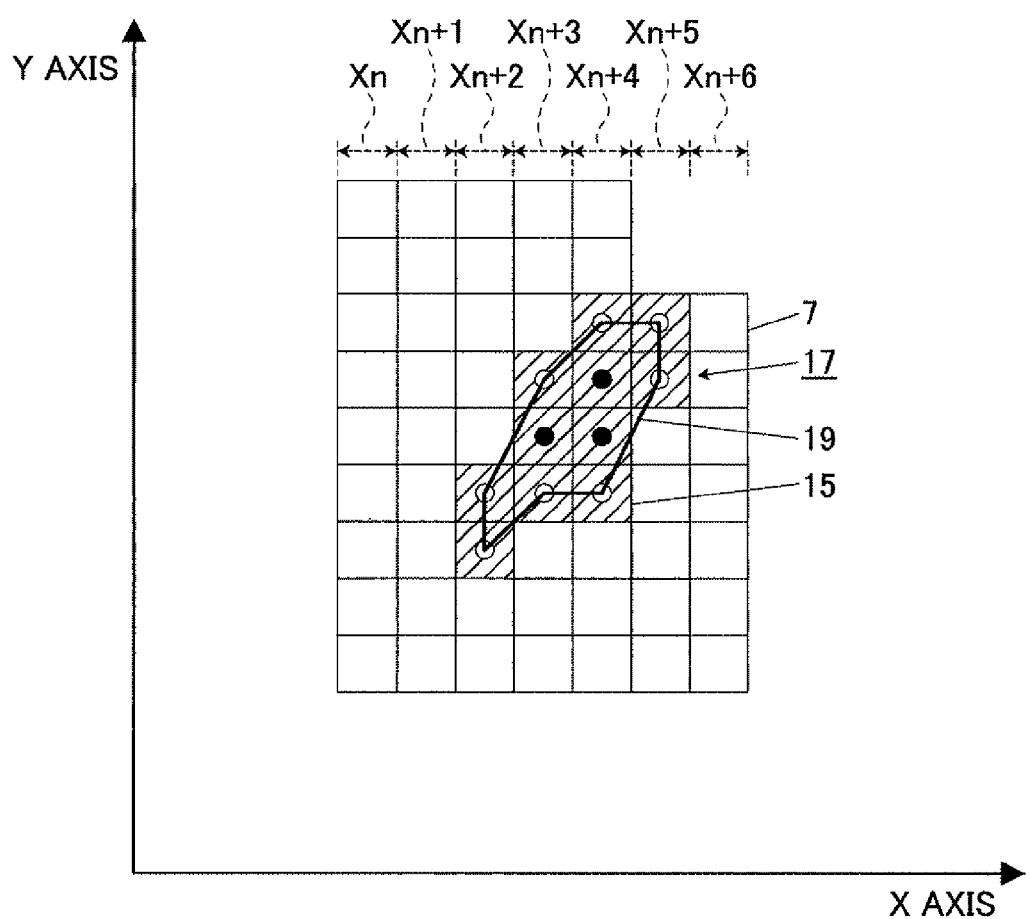
FIG. 17 is an enlarged view of the vicinity of the concentrated defect distribution in FIG. 15.

FIG. 17 is an enlarged view of the vicinity of the concentrated defect distribution 17 of FIG. 16. In FIG. 17, the chip border lines extending along the Y axis direction are regarded as the dividing straight lines so that the area of the coordinate plane is divided into areas, which are divided areas Xn thought Xn+6 (n: an integer).

In this case, when the concentrated defect distribution representative point area 19 corresponding to the concentrated defect distribution 17 is to be obtained by obtaining the representative points (white circles) using the center points (black circles and white circles) of the centers of the chips 7 and the defective chips 15, a large part of the area of the defective chips 15 of the concentrated defect distribution 17 protrudes from the area of the concentrated defect distribution representative point area 19.

When this is not desirable, the positional information indicating the chips 7 of the wafer test result data is replaced by the positional information indicating the four corners of the chips 7 and then the representative points of the concentrated defect distribution 17 are obtained.

Figure 18:
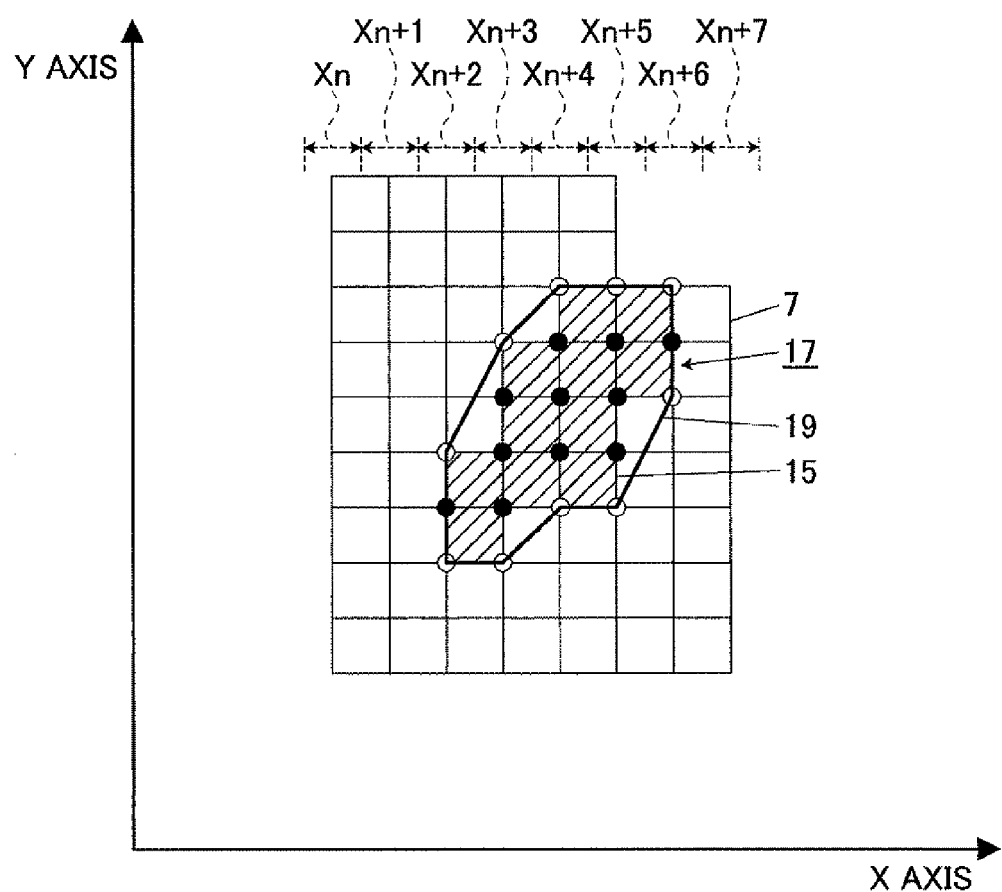
FIG. 18 is a drawing illustrating the representative points and the concentrated defect distribution representative point area when the positional information is replaced by the four (4) corners of the chips.

FIG. 18 illustrates the representing points and the concentrated defect distribution representative point area 19 when the positional information indicating the chips 7 of the wafer test result data is replaced by the positional information indicating the four corners of the chips 7. In FIG. 18, the straight lines extending in the Y axis direction are regarded as the dividing straight lines and the area of the coordinate plane is divided into the divided areas Xn through Xn+7 (n: an integer).

As illustrated in FIG. 18, when the concentrated defect distribution representative point area 19 corresponding to the concentrated defect distribution 17 is obtained by obtaining the representative points (white circles) using the positional information (black circles and white circles) indicating the four (4) corners of the defective chips 15, there is no part of the area of the defective chips 15 of the concentrated defect distribution 17 that protrudes from the area of the concentrated defect distribution representative point area 19.

In the above embodiment, as illustrated in, for example, FIG. 2, the determination area 5 is set on a part of upper right-hand side when the wafer 1 is set in a manner such that the notch 3 of the wafer 1 is arranged on the lower side. However, the determination area 5 may be set at any position and area.

For example, the determination area 5 may be set as the upper half part or the right half part of the wafer 1 assuming the notch 3 is arranged on the lower (bottom) side.

Further, it is not always necessary that the determination area 5 has a frame shape. For example, the determination area 5 may have a shape other than the frame shape and may be expressed as an area defined by X>0 and Y>0 or an area defined by X<2 in the XY coordinate plane.

Figure 19:
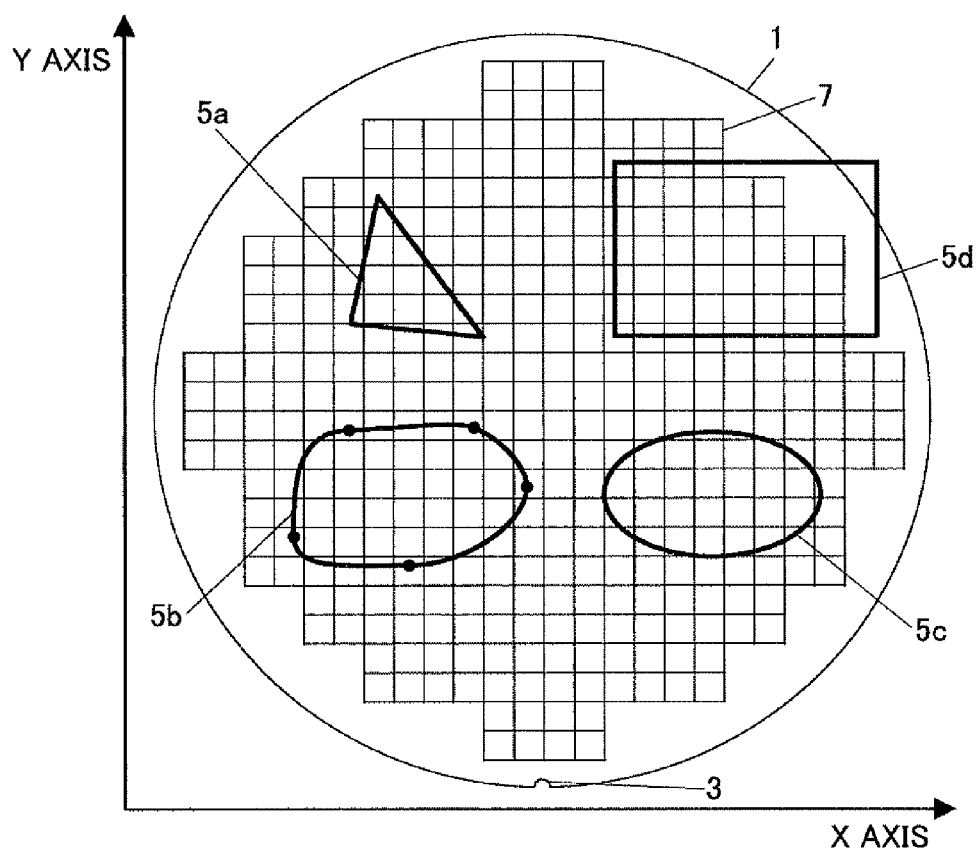
FIG. 19 is a drawing illustrating examples of the determination areas.

FIG. 19 illustrates some examples of the determination area 5. As illustrated in FIG. 19, the determination area 5 may be a determination area 5a having a triangular shape, a determination area 5b formed by connecting the plural points with smooth curves, a determination area 5c having an elliptic shape, a determination area 5d including an area protruding from the wafer 1 or the like.

Next, a specific use according to an embodiment of the present invention is described with reference to FIGS. 20 through 24.

Figure 20:
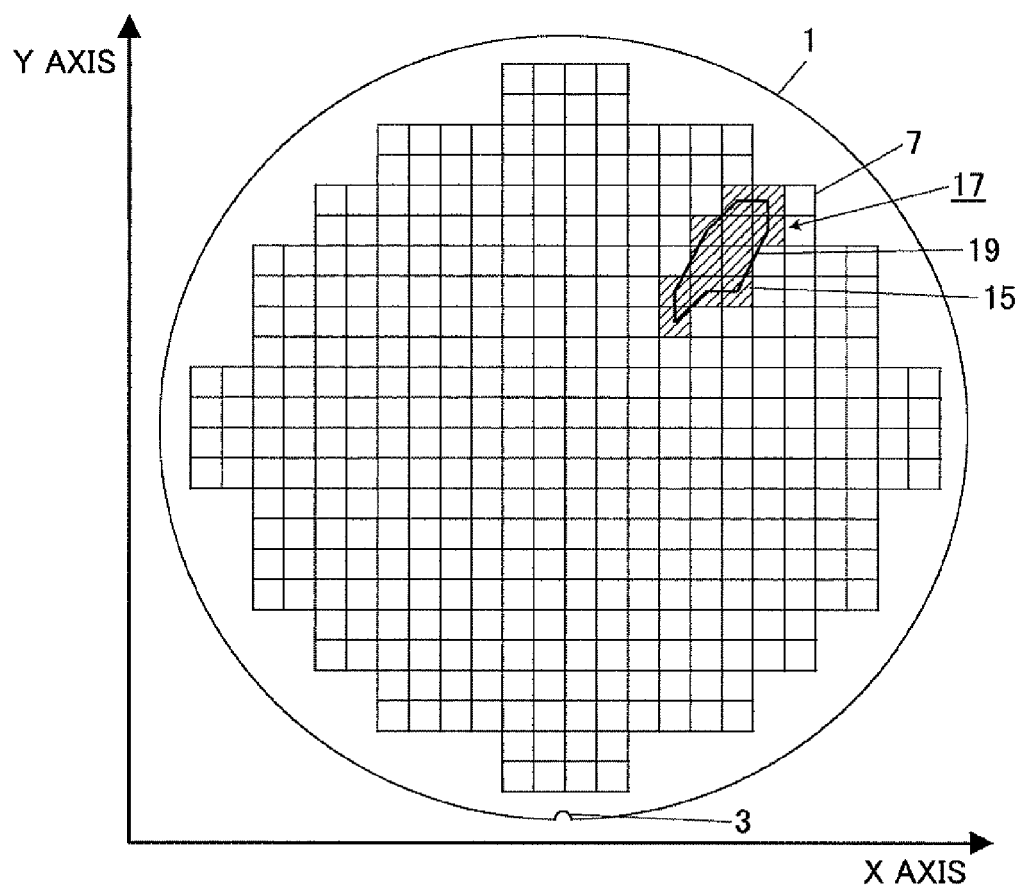
FIG. 20 is a drawing illustrating a wafer test result on a coordinate plane.

FIG. 20 illustrates the wafer test result data on the coordinate plane. Specifically, FIG. 20 illustrates the concentrated defect distribution 17 and the concentrated defect distribution representative point area 19 corresponding to the concentrated defect distribution 17, the concentrated defect distribution 17 including the plural defective chips 15.

Figure 21:
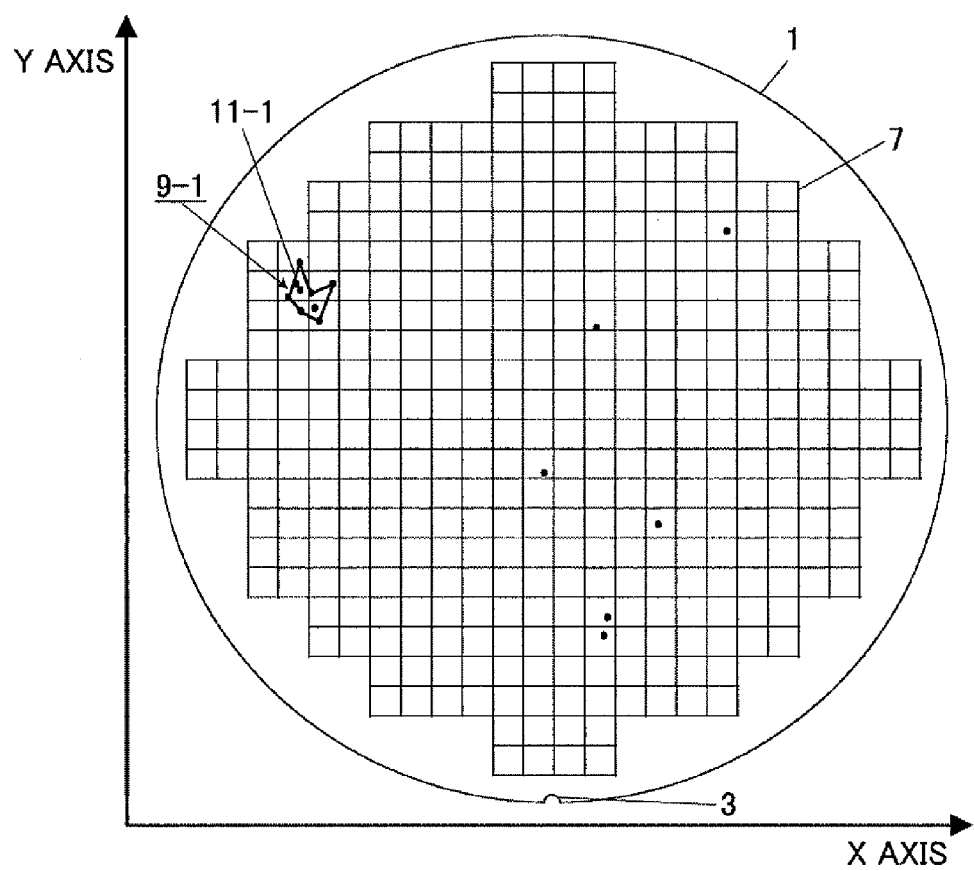
FIG. 21 is a drawing illustrating a defect inspection result of a metal 1 forming process on the coordinate plane.

FIG. 21 illustrates the defect inspection result data of a metal 1 forming process on the coordinate plane. Specifically, FIG. 21 illustrates data points (black circles) indicating the pattern defect positions, the concentrated pattern defect distribution 9-1, and the concentrated pattern defect distribution representative point area 11-1 corresponding to the concentrated pattern defect distribution 9-1.

Figure 22:
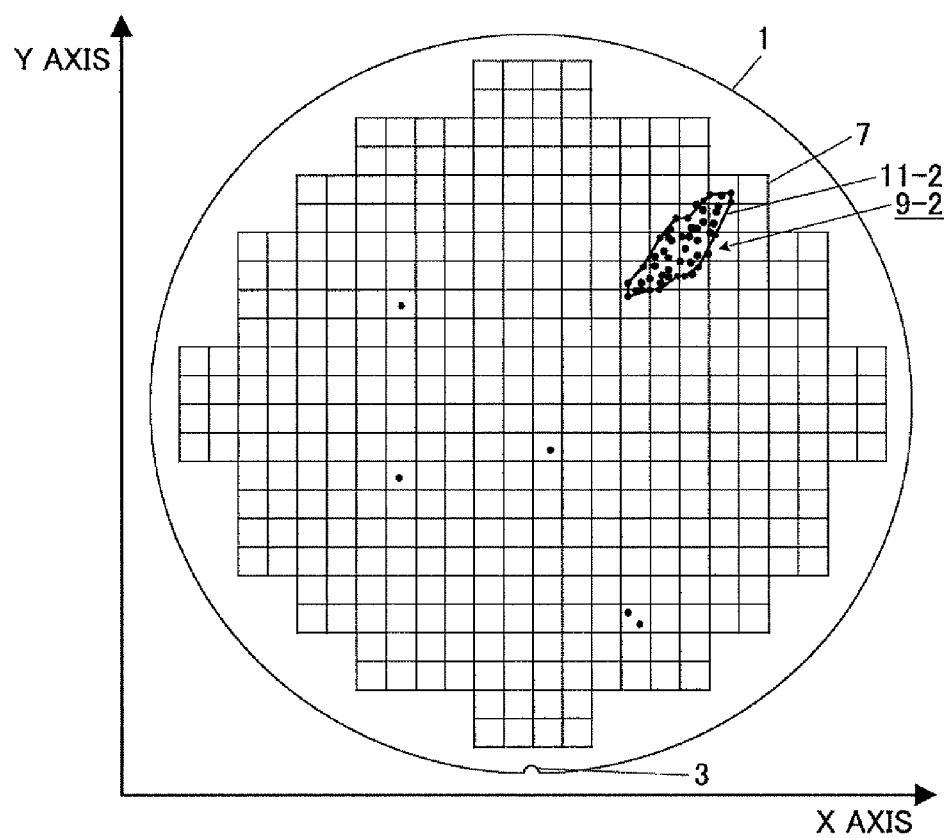
FIG. 22 is a drawing illustrating a defect inspection result of a metal 2 forming process on the coordinate plane.

FIG. 22 illustrates the defect inspection result data of a metal 2 forming process on the coordinate plane. Specifically, FIG. 22 illustrates data points (black circles) indicating the pattern defect positions, the concentrated pattern defect distribution 9-2, and the concentrated pattern defect distribution representative point area 11-2 corresponding to the concentrated pattern defect distribution 9-2.

Figure 23:
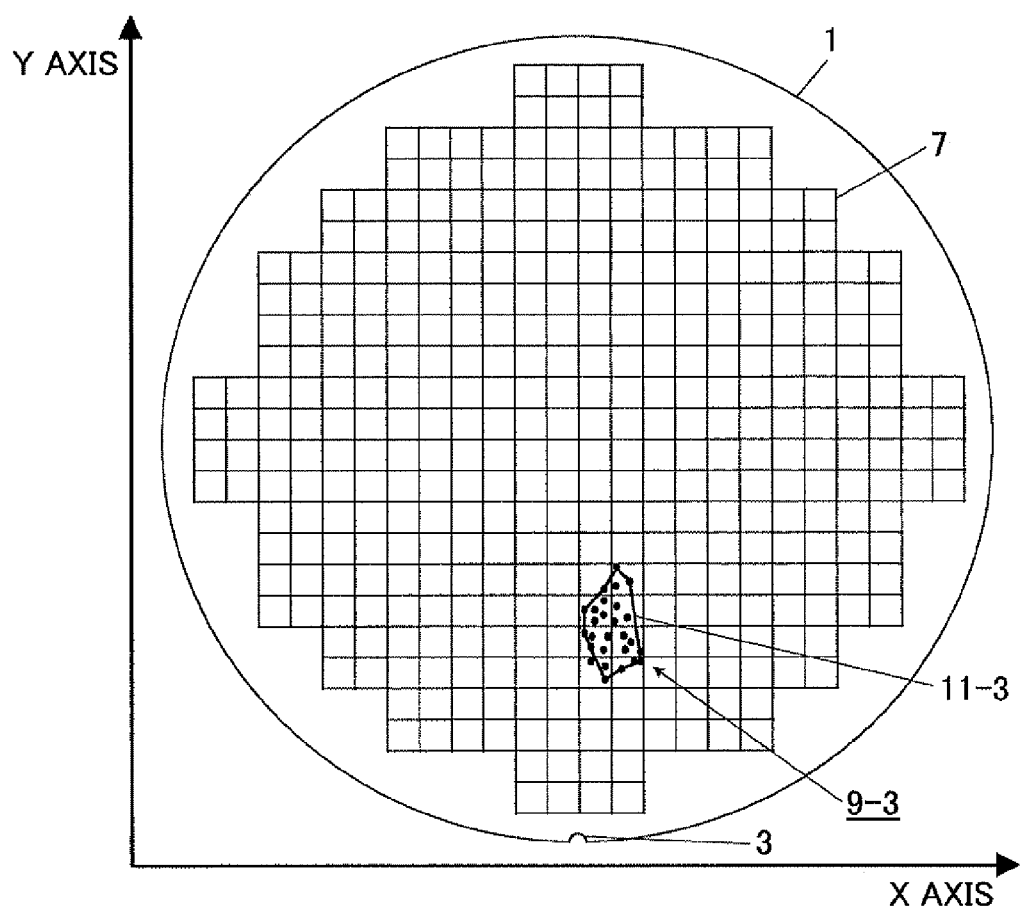
FIG. 23 is a drawing illustrating a defect inspection result of a metal 3 forming process on the coordinate plane.

FIG. 23 illustrates the defect inspection result data of a metal 3 forming process on the coordinate plane. Specifically, FIG. 23 illustrates data points (black circles) indicating the pattern defect positions, the concentrated pattern defect distribution 9-3, and the concentrated pattern defect distribution representative point area 11-3 corresponding to the concentrated pattern defect distribution 9-3.

Figure 24:
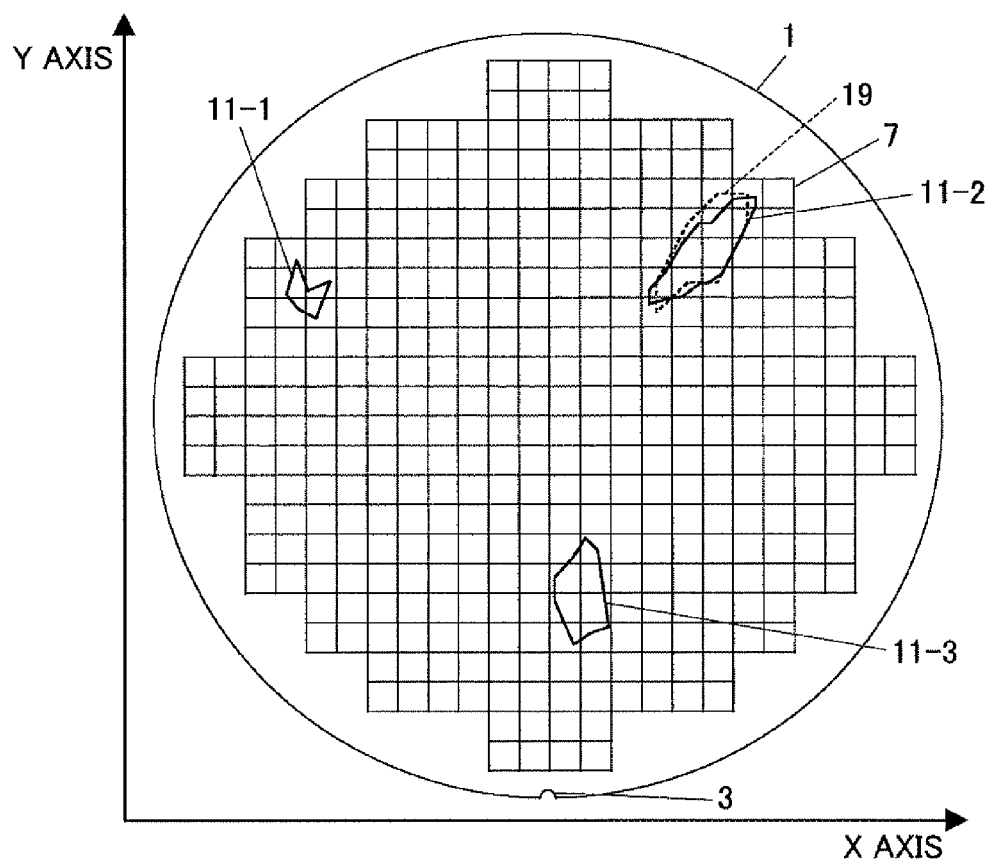
FIG. 24 is a drawing illustrating the concentrated pattern defect distribution representative point areas and the concentrated detective distribution representative point area of FIGS. 20, 21, 22, and 23 in a manner such that the areas are overlapped with each other.

In FIG. 24, the concentrated defect distribution representative point area 19 and the concentrated pattern defect distribution representative point areas 11-1, 11-2 and 11-3 of FIGS. 20, 21, 22, and 23, respectively, are illustrated in an overlapped manner. Further, in FIG. 24, the contour of the concentrated defect distribution representative point area 19 is indicated in a dotted line.

In the wafer test result, when the concentrated defect distribution 17 as illustrated in FIG. 20 is obtained, by setting the concentrated defect distribution representative point area 19 corresponding to the concentrated defect distribution 17 as the determination area, it may be determined that the concentrated pattern defect distribution representative point area is the wafer information to be determined for each of the pattern defect inspection results of the metal forming processes. When one of the defective pattern defect inspection results of the metal forming processes is defective, the defective pattern defect inspection result includes the concentrated pattern defect distribution representative point area overlapping the concentrated defect distribution representative point area 19 (determination area 5) as the concentrated pattern defect distribution representative point area 11-2 of the metal 2 forming process. By using this feature, it may become possible to select the wafer information to be determined which includes the information indicating the cause of the occurrence of the concentrated defect distribution 17.

The steps of the embodiment described above may be realized by executing a program using a computer, the program being generated for the execution of the steps described above.

Further, as a function of the program, it may be preferable to draw the distributed defect distribution representative point areas or the concentrated pattern defect distribution representative point areas of the plural wafer information having been determined as the wafer information on one coordinate plane, and allow to select unnecessary distributed defect distribution representative point areas or the concentrated pattern defect distribution representative point areas so as to remove those wafer information from all the wafer information. By having this function, it may become possible to adequately select the wafer information.

Figure 25:
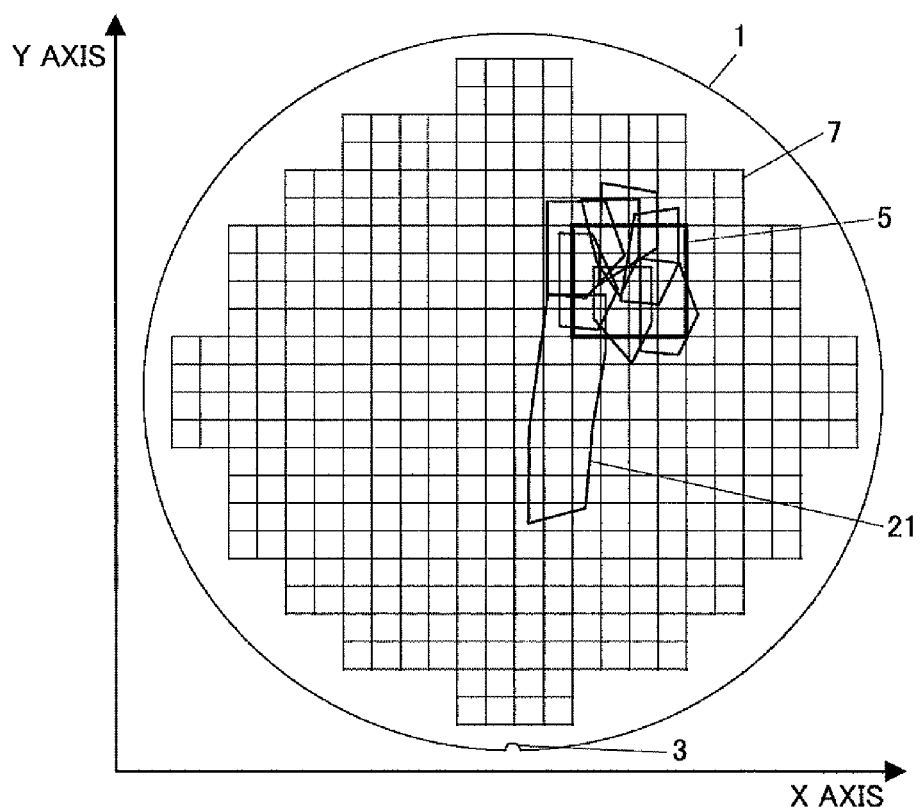
FIG. 25 is a drawing illustrating the concentrated pattern defective distribution representative point areas and the determination area on one coordinate plane, the concentrated pattern defective distribution representative point areas corresponding to the concentrated pattern defect distributions of plural wafer information.

Namely, as illustrated in FIG. 25, when it is desirable to remove the wafer information having the concentrated pattern defect distribution corresponding the concentrated pattern defect distribution representative point area having the distribution in an area far from the determination area 5 like the concentrated pattern defect distribution representative point area 21 in FIG. 25 from the wafer information, it may be preferable to display a figure illustrating the concentrated pattern defect distribution representative point areas of the plural wafer information on one coordinate plane, and allow to select a peculiar concentrated pattern defect distribution representative point area using a mouse or the like so as to remove the wafer information having the concentrated pattern defect distribution corresponding to the selected peculiar concentrated pattern defect distribution representative point area. Further, when the first ratio threshold value described with reference to FIG. 8 and the second ratio threshold value described with reference to FIG. 9 are used, it may become possible to automatically remove the wafer information corresponding to the concentrated pattern defect distribution representative point area 21 in FIG. 25.

Next, a modified example in step of selecting the representative points is described.

Figure 26:
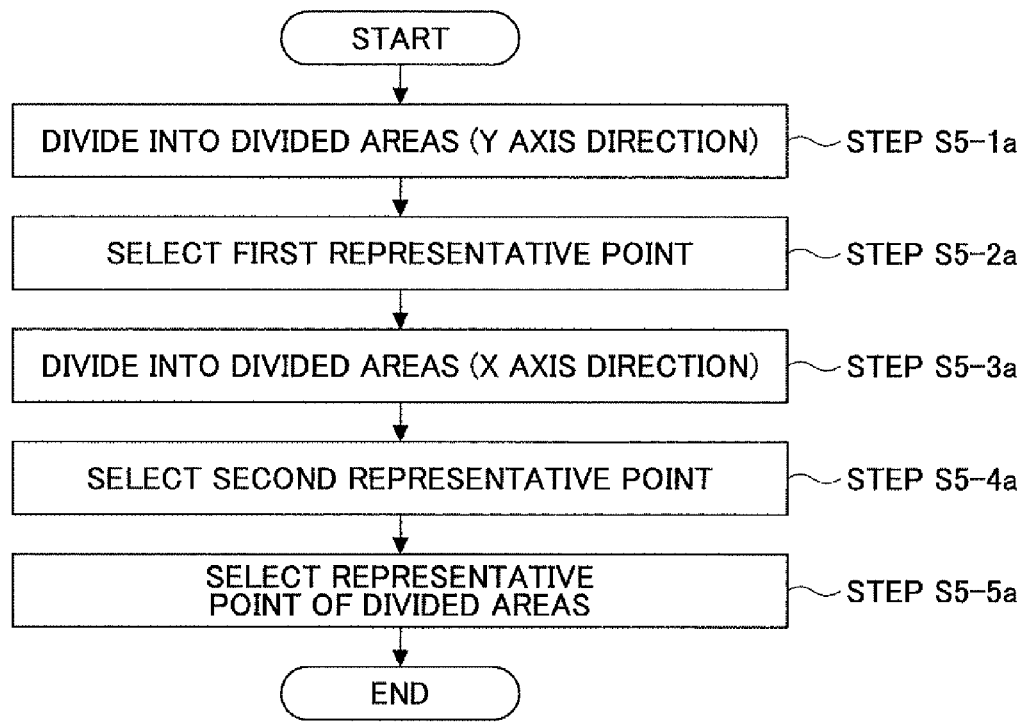
FIG. 26 is a flowchart illustrating a modified example of the distribution representative point selection step.
Figure 27:
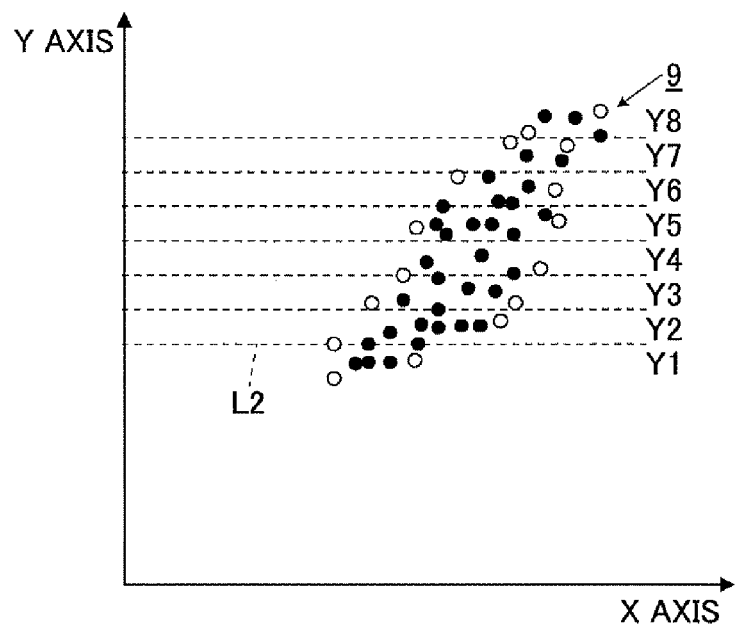
FIG. 27 is a view of the concentrated pattern defect distribution of FIG. 5, the view including second dividing straight lines along the X axis on the coordinate plane to divide the area of the concentrated pattern defect distribution into eight (8) areas.
Figure 28:
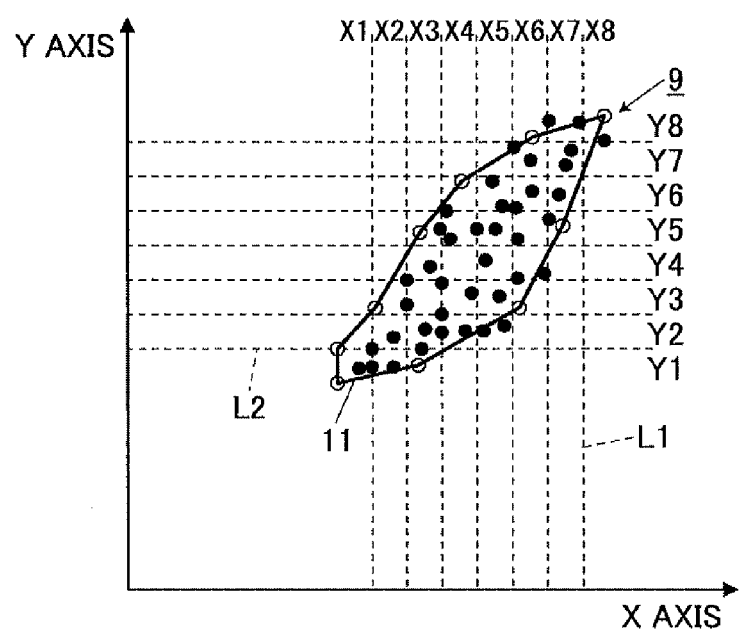
FIG. 28 is a drawing illustrating the dividing straight lines along the Y and the concentrated pattern defect distribution representative point area of the concentrated pattern defect distribution on the coordinate plane of FIG. 27.

FIG. 26 is a flowchart illustrating a modified example of step of selecting the representative points. FIG. 27 illustrates the concentrated pattern defect distribution 9 of FIG. 5 and second dividing straight lines extending along the X axis direction so as to divide the area into eight (8) areas on the coordinate plane. In FIG. 28, the dividing straight lines extending along the Y axis direction and the concentrated pattern defect distribution representative point area corresponding to the concentrated pattern defect distribution 9 are added to the coordinate plane of FIG. 27.

With reference to FIGS. 5, 26, 27, and 28, the modified example of the step of selecting the representative points is described.

Steps S5-1a and Ss-2a: Similar to steps S5-1 and S5-2 described with reference to FIGS. 4 and 5, by setting the dividing straight lines L1 extending in the direction parallel to the Y axis (one of the coordinate axes) direction, the maximum value side representative points and the minimum value side representative points are selected. Then the selected representative points are set as the first representative point candidates (see FIG. 5). In FIG. 5, the data points of the first representative point candidates are displayed in white circles, and the data points other than the first representative point candidates are displayed in black circles.

Step S5-3a: as illustrated in FIG. 27, the distribution area of the data points is divided into, for example, eight divided areas using the second dividing straight lines L2 extending in the direction parallel to the Y axis (the other coordinate axis) direction. In this case, seven second dividing straight lines L2 parallel to each other are used. However, the number of the divided areas is not limited to eight (8). Two or more divided areas may adequately determined.

Step S5-4a: Next, for each of the divided areas Y1 through Y8, the data points positioned at the far end position along the two directions parallel to the extending direction of the second dividing straight lines L2 are selected as the second representative point candidate of the data point distribution area. In this case, in each of the divided areas Y1 through Y8, the data point having the maximum value in the X axis coordinate is selected as the maximum value side representative point, and the data point having the minimum value in the X axis direction is selected as the minimum value side representative point. The, those representative points are set as second representative point candidates. In FIG. 27, the data points of the second representative point candidates are displayed in white circles, and the data points other than the second representative points are displayed in black circles.

Step S5-a: The data points that have been set as the first representative point candidates in step S5-2a and that have been set as the second representative point candidates in step S5-4a are selected as the representative points (see FIG. 28). In FIG. 28, the data points of the representative points are displayed in white circles, and the data points other than the representative points are displayed in black circles.

As determination steps S6 and S20 illustrated in FIGS. 1 and 7, respectively, for the concentrated pattern defect distribution 9 and the representative points illustrated in FIG. 28, the concentrated pattern defect distribution representative point area 11 illustrated in FIG. 28 is defined by connecting from the representative point as the start point to the next representing point of the adjacent area with a line and further connecting in the same manner in the clockwise or counterclockwise direction.

To define the concentrated pattern defect distribution representative point area 11 indicating the contour of the concentrated pattern defect distribution 9, it is necessary to sequentially connect the representative points in a manner such that none of the lines are crossed over each other. As a method to avoid crossing the lines, the following method may be used.

When a data point obtained as the maximum value side first representative point candidate in the divided area X1 is the representative point, the data point is set as the start point. Otherwise, as the start point, the data point is searched for sequentially from the divided area X2 to the divided area X8, the data point being the maximum value side first representative point candidate and the representative point. After the start point is determined (searched for), the data points that are the maximum value side first representative point candidate and that are the representative point are sequentially searched for (detected) from the divided area Xa ("a": a natural number from 2 to 8) including the representative point as the start point to the divided area X8, and the start point and the detected points are sequentially connected with lines. Next, the data points that are the minimum value side first representative point candidate and that are the representative points are sequentially searched for (detected) from the divided area X8 to the divided area X1, and the detected points and the start point are sequentially connected with lines. By doing this, the area of the concentrated pattern defect distribution representative point area 11 is defined. The lines used for defining the area of the concentrated pattern defect distribution representative point area 11 may be straight lines connected between the representative points or smooth curve line passing through the representative points.

As described above, in step of selecting the representative points, it may become possible to appropriately select the representative points for defining the distribution representative point area corresponding to the distribution area of the data points.

Further, depending on the relationship between the distribution status of the data points and the setting of the divided areas, there may be a case where there is only one data point in any of the divided areas X1 through X8 in the X axis direction and the divided areas Y1 through Y8 in the Y axis direction. In this case, in the divided area where there is only one data point, the data point may be selected as the maximum value side representative point candidate as well as the minimum value side representative point candidate.

Further, in steps of selecting the representative points described with reference to flowchart of FIG. 4 or 26, it is assumed the divided areas X2 through X7 have the same widths as each other. In the same manner, in steps of selecting the representative points described with reference to flowchart of FIG. 26, it is assumed the divided areas Y2 through Y7 have the same widths as each other. However, the present invention is not limited to this configuration. The widths of the divided areas may be different from each other. Further, the number of the divided areas is not limited to a specific number. The number of the divided areas may be any number more than one.

Further, in the step of selecting the representative points, the dividing straight lines L1 extend in the direction parallel to the Y axis direction and the second dividing straight lines L2 extend in the direction parallel to the X axis direction. However, the present invention is not limited to this configuration. For example, the dividing straight lines L1 may extend in the direction parallel to the X axis direction and the second dividing straight lines L2 may extend in the direction parallel to the Y axis direction.

Further, the dividing straight line L1 and the second dividing straight line L2 may not be orthogonal to each other. Further, at least one of the dividing straight line L1 and the second dividing straight line L2 may not be parallel to any direction of the coordinate axes directions in the coordinate plane.

Figure 29:
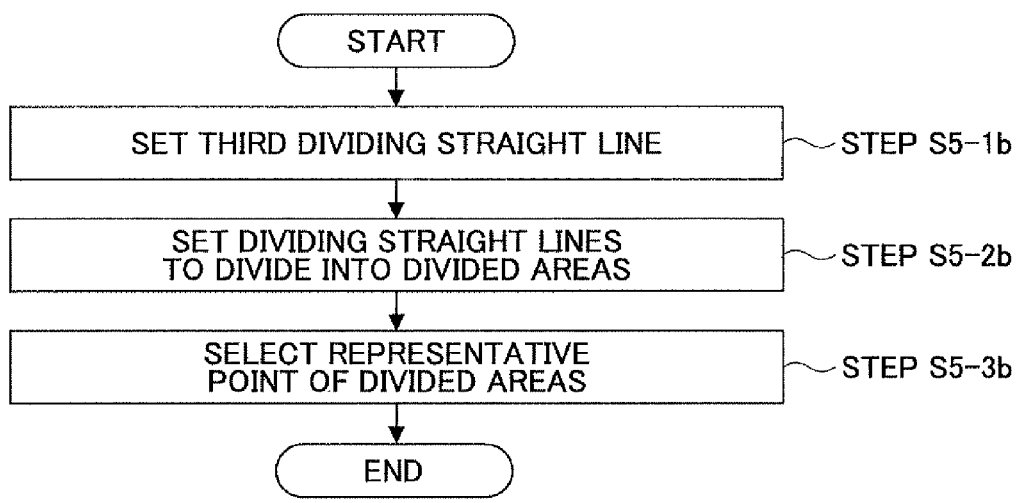
FIG. 29 is a flowchart illustrating another modified example of the distribution representative point selection step.
Figure 30:
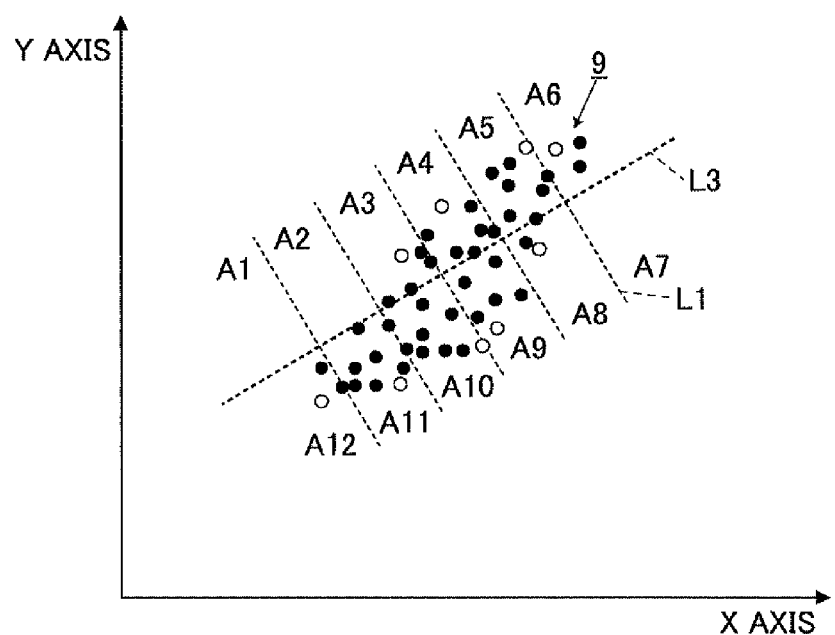
FIG. 30 is a drawing illustrating a dividing straight line and third dividing straight lines to divide the distribution area of the data points into twelve (12) areas on the coordinate plane of the concentrated pattern defect distribution of FIG. 5.
Figure 31:
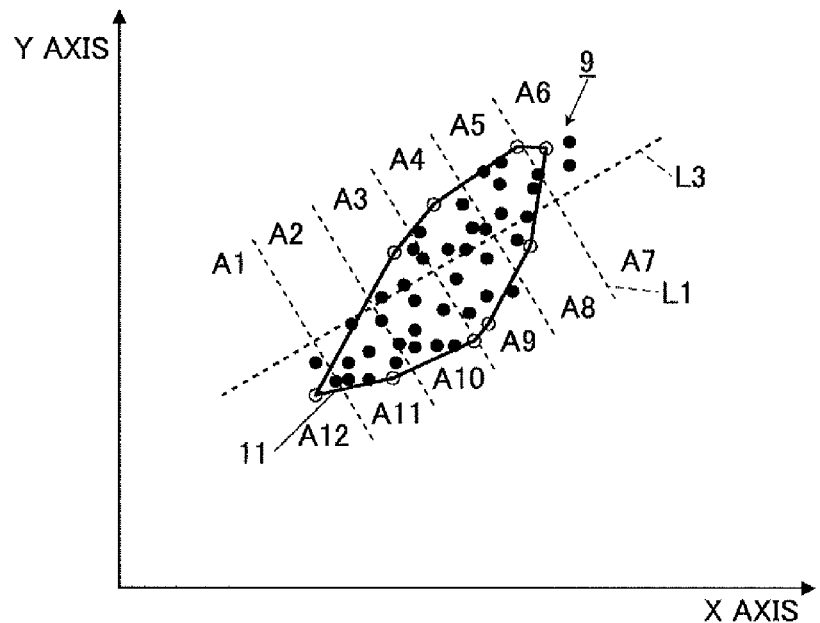
FIG. 31 is a drawing further illustrating the concentrated pattern defect distribution representative point area on the coordinate plane of FIG. 30.

FIG. 29 is a flowchart illustrating another modified example of the step of selecting the representative points. FIG. 30 illustrates a third dividing straight line L3 added to the coordinate plane on which the concentrated pattern defect distribution 9 of FIG. 5 is displayed. The third dividing straight line L3 is provided so as to divide the distribution area of the data points into 12 divided areas. FIG. 31 illustrates the concentrated pattern defect distribution representative point area 11 added to the coordinate plane of FIG. 30. With reference to FIGS. 29 through 31, the modified example of the step of selecting the representative points is described.

Step S5-1b: as illustrated in FIG. 30, the third dividing straight line L3 crossing the distribution area of the data points is provided. Any line may be used as the third dividing straight line L3 crossing the distribution area. In FIG. 30, the third dividing straight line L3 is provided so as to form angles relative to the X axis and the Y axis. However, the third dividing straight line L3 may be provided so as to be parallel to the X axis or the Y axis.

Step S5-2b: Next, the dividing straight lines L1 orthogonal to the third dividing straight line L3 are provided so as to further divide the distribution area of the data points. Specifically, in this embodiment, as illustrated in FIG. 30, five dividing straight lines L1 orthogonal to the third dividing straight line L3 are provided, so that the distribution area of the data points is divided into twelve (12) divided areas A1 through A12.

Step S5-3b: In each of the twelve (12) divided areas A1 through A12, the data points having the greatest distance from the third dividing straight line L3 are selected (obtained) as the representative points. In FIG. 30, the representative points of the twelve (12) divided areas are displayed in white circles. In the divided areas A1, A2, and A7, there are no data points. As a result, no representative points are obtained in those divided areas.

As determination steps S6 and S20 illustrated in FIGS. 1 and 7, respectively, for the concentrated pattern defect distribution 9 and the representative points illustrated in FIG. 30, the concentrated pattern defect distribution representative point area 11 illustrated in FIG. 31 is defined by connecting from the representative point as the start point to the next representing point of the adjacent area with a line and further connecting in the same manner in the clockwise or counterclockwise direction. As an exemplary method to avoid crossing the lines defining the concentrated pattern defect distribution representative point area 11, there is a method in which the representative lines are sequentially connected in the order of the divided areas A1, A2, A3, . . . , A10, A11, and A12.

As described above, even in the step of selecting the representative points, the representative points for defining the distribution representative point area corresponding to the distribution area of the data points may be appropriately selected.

Further, in a case where there is the divided area including no representative data (i.e., the divided area including no data point), when there are two or more data points in the dividing area opposite to the divided area including no representative data across the third dividing straight line L3, the data point closest to the third dividing straight line L3 from among the two or more data points in the dividing area may be set as the representative point of the divided area including no representative data.

Figure 32:
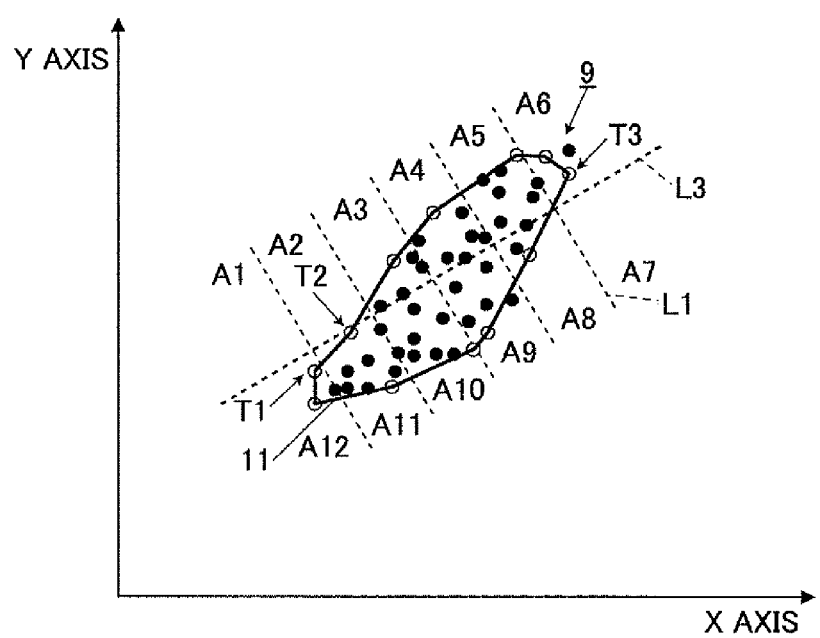
FIG. 32 is a drawing illustrating a result of defining the concentrates pattern defect distribution representative area by adding the representative points to the data point distribution area of FIG. 30.

FIG. 32 illustrates the concentrated pattern defect distribution representative point area 11 as a result of additional representative points added to the data point distribution area of FIG. 30.

In step S5-3b of the flowchart of FIG. 29, for each of the divided areas A1 through A12, the data point having the greatest distance from the third dividing straight line L3 is obtained as the representative point, and the representative points of the divided areas A1, A2, and A7 are obtained. In this case, the process of obtaining the representative points of the distributed areas A1 through A12 may be performed before or after the process of obtaining the representative points for the divided areas where there is no data point is performed.

As illustrated in FIG. 32, there is no data point in the divided area A1, and there are two or more data points in the divided areas A12 facing the divided area A1 across the third dividing straight line L3. Therefore, in the divided area A12, the data point closest to the third dividing straight line L3 is selected as the representative point T1 of the divided area A1.

Further, there is no data point in the divided area A2, and there are two or more data points in the divided area A11 facing the divided area A2 across the third dividing straight line L3. Therefore, in the divided area A11, the data point closest to the third dividing straight line L3 is selected as the representative point T2 of the divided area A2.

Further, there is no data point in the divided area A7, and there are two or more data points in the divided area A6 facing the divided area A7 across the third dividing straight line L3. Therefore, in the divided area A6, the data point closest to the third dividing straight line L3 is selected as the representative point T3 of the divided area A7.

After that, as determination steps S6 and S20 illustrated in FIGS. 1 and 7, respectively, for example, the concentrated pattern defect distribution representative point area 11 illustrated in FIG. 32 is defined by connecting from the representative point as the start point to the next representing point of the adjacent area with a line and further connecting in the same manner in clockwise or counterclockwise direction.

As describe above, by setting the representative points T1, T2, and T3 as the representing points of the divided areas A1, A2, and A7, respectively, and by sequentially connecting the representing points of the divided areas A1, A2, A3, ..., A10, A11, and A12, with lines, the lines of the concentrated pattern defect distribution representative point area 11 may be formed without being crossed to each other.

Further, in the step of selecting the representative points described with reference to FIG. 29, as the third dividing straight line L3, a regression straight line of the data points may be used.

Figure 33:
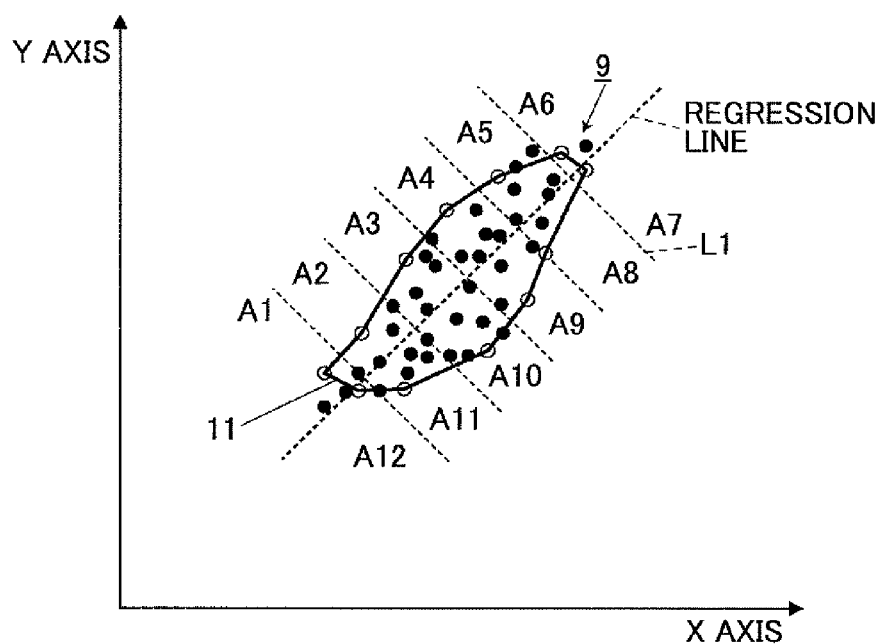
FIG. 33 is a drawing illustrating the dividing straight lines, a regression straight line, and the distribution representative point region on the coordinate plane of the concentrated pattern defect distribution of FIG. 5, the dividing straight lines and the regression straight line being for dividing the distribution area of the data points into twelve (12) areas.

FIG. 33 further illustrates the dividing straight lines L1 and the regression straight line to divide the distribution area of the data points into twelve (12) divided areas and the concentrated pattern defect distribution representative point area 11 on the coordinate plane on which the concentrated pattern defect distribution 9 illustrated in FIG. 5 is displayed.

Further, in the step of selecting the representative points, the maximum value and the minimum value in one of the coordinate axes of the coordinate plane of the data points in the distribution area are obtained. Then, the points that are on the regression straight line and that have the obtained maximum value and the minimum value are obtained. Then, the obtained points are set as the additional representative points.

Figure 34:
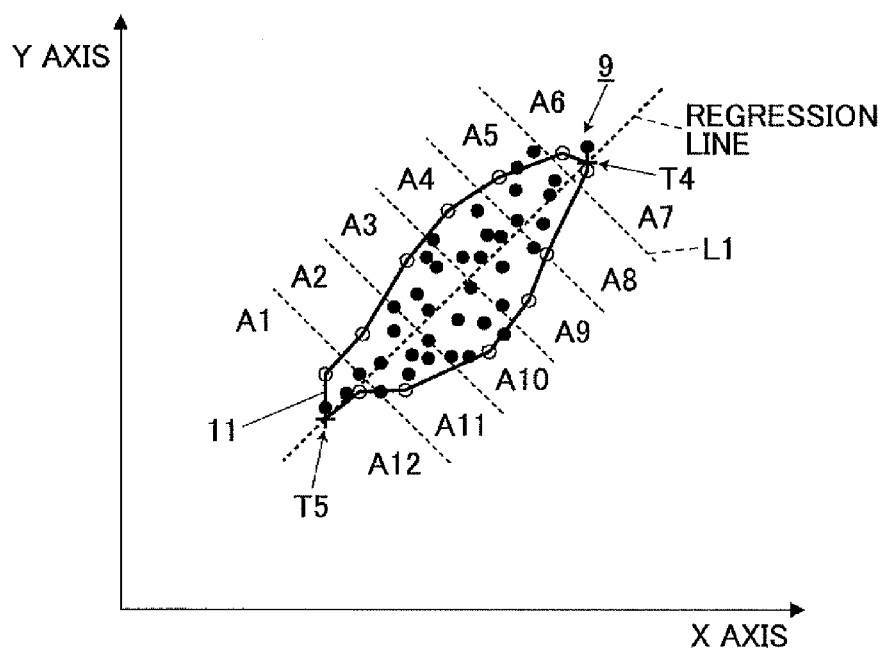
FIG. 34 is a drawing defining the distribution representative point area by adding the representative points on the regression straight line to the representative points of FIG. 33.

FIG. 34 illustrates the additional representative points on the regression straight line added to the representative points illustrated in FIG. 33 so as to define the concentrated pattern defect distribution representative point area 11. In this example, with respect to the X axis, the maximum value and the minimum value of the distribution area of the data points are obtained. Then the points that are on the regression straight line and that have the obtained maximum value and minimum value are set as the representative points T4 and T5 (points marked "+" in FIG. 34), respectively. To prevent the lines defining the concentrated pattern defect distribution representative point area 11 from being crossed with each other, it may be necessary to connect the representative points with the lines in the order of the representative point of divided area A1, the representative point of divided area A2, ..., the representative point of divided area A5, the representative point of divided area A6, the representative point T4, the representative point of divided area A7, the representative point of divided area A8, ..., the representative point of divided area A11, the representative point of divided area A12, and the representative point T5.

Further, similar to the above, with respect to the Y axis, the maximum value and the minimum value of the distribution area of the data points may be obtained. Then the points that are on the regression straight line and that have the obtained maximum value and minimum value may be set as the representative points.

When the representative point is set on the regression straight line, the representative point may not be obtained in the end divided areas or the representative point of the end divided areas may be ignored.

Figure 35:
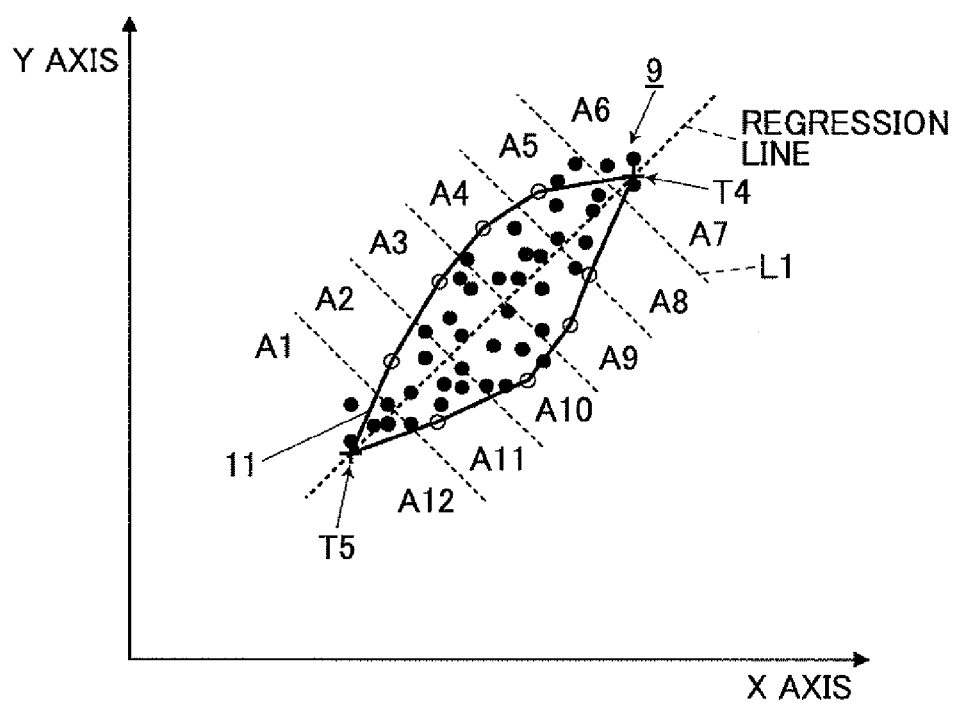
FIG. 35 is a drawing defining the distribution representative point area by adding the representative points on the regression straight line to the representative points of FIG. 33 and ignoring the representative points in the end of the divided areas.

FIG. 35 illustrates the representative points on the regression straight line added to the representative points of FIG. 33, so that the distribution representative point area is defined by ignoring the representative points of the end divided areas.

In FIG. 35, the distribution representative point area is defined by adding the representative points T4 and T5 on the regression straight line and ignoring the representative points of the end divided areas A1, A6, A7, and A12. Therefore, the representative points of the end divided areas A1, A6, A7, and A12 are displayed in black circles similar to the data points which are other than the representative points. Further, in this case, the process of obtaining the representative points of the end divided areas A1, A6, A7, and A12 may be or may not be performed.

In the above description of the step of selecting the representative points, a method is described where the maximum value and the minimum value in one of the coordinate axes of the coordinate plane of the data points in the distribution area are obtained, the points that are on the regression straight line and that have the obtained maximum value and the minimum value are obtained, the obtained points are set as the additional representative points, and the regression straight line is used as the third dividing straight line. However, the method is not limited to the above step. Namely, the above method may also be applied to any of the steps of selecting the representative points described with reference to the flowcharts of FIGS. 4, 26, and 29. Namely, in any of the steps of selecting the representative points, the maximum value and the minimum value in one of the coordinate axes of the coordinate plane of the data points in the distribution area are obtained, the points that are on the regression straight line and that have the obtained maximum value and the minimum value are obtained, and the obtained points are set as the additional representative points, and the regression straight line is used as the third dividing straight line.

Each of the steps in the embodiments described above may be realized by creating a program for executing the steps and causing the computer to execute the created program.

According to an embodiment of the present invention, there is provided an identification method of identifying a data point distribution area on a coordinate plane. The identification method includes a distribution representative point selection step of dividing an area on the coordinate plane into two or more divided areas by providing and using one dividing straight line or plural dividing straight lines parallel to each other, plural data being expressed as data points on the coordinate plane, the plural data constituting a data group to be determined, each of the plural data including two variables as a pair, the dividing straight line or the plural dividing straight lines crossing the data point distribution area, the data point distribution area being a distribution are of the data points, and selecting, in each of the divided areas, from among the data points in the divided area, an outermost data point in each of two directions as representative points of the data point distribution area, the two directions being parallel to an extending direction of the dividing straight line or plural dividing straight lines; and a determination step of determining whether there is an overlapping area where a distribution representative point area overlaps a determination area, the distribution representative point area being defined by connecting the representative points with lines, the determination area being a specific area set on the coordinate plane, and further determining, when determining that there is the overlapping area, that the data group to be determined is a relevant data group.

Herein, the coordinate plane may be an orthogonal coordinate plane or an oblique coordinate plane.

Further, the data point distribution area may be defined by the circumferential lines and the inside of the circumferential lines when all the data points are connected to each other with lines.

Further, the number of divided areas on the coordinate plane is two or more.

Further, the data point on the border line between two adjoining divided areas may be treated as the data point of each of the two divided areas or the data point of either one of the two divided areas. In the latter case, it may be defined in advance whether the data point on the border line is to be treated as the data point of which of the adjoining divided areas. For example, when the area of the coordinate plane is divided into plural divided areas by using plural straight lines orthogonal to the Y axis, it is determined in advance that the data point on the border line (straight line) is to be treated as the data point on the divided area having smaller Y coordinate value.

Further, the data group to be determined may be any one of pattern defect inspection result data, particle inspection result data, and wafer test result data in a semiconductor device manufacturing process. However, the data group to be determined is not limited to those data.

Further, the identification method of identifying a data point distribution area on a coordinate plane may further include a representative point information registration step of associating and registering information of the representative points acquired in the distribution representative point selection step with information to be used to identifying the data group to be determined into a database, in which the representative point information registration step is performed before the determination step is performed, and in the determination step, it is determined whether there is the overlapping area by reading the information of the representative points associated with the information to be used to identifying the data group to be determined from the database.

Further, in the representative point information registration step, characteristic information may be associated with the information to be used to identifying the data group to be determined and stored in the database, the characteristic information including a distribution range of the data point distribution area, a distribution range of the distribution representative point area, and at least one of an area, a roundness rate, and a data point distribution density of the distribution representative point area, and in the determination step, after making a short list of the data group to be determined based on the characteristic information, it may be determined whether there is the overlapping area.

Herein, the information indicating the distribution range of the data point distribution area is expressed by the maximum value and the minimum value in the X axis and the maximum value and the minimum value in the Y axis from among the XY coordinate values of the data points included in the data point distribution area or by the maximum r value, the minimum r value, the maximum θ value, and the minimum θ value of the data point distribution area of the polar coordinate values.

Further, the information indicating the distribution range of the distribution representative point area is expressed by the maximum value and the minimum value in the X axis and the maximum value and the minimum value in the Y axis from among the XY coordinate values of the data points included in the distribution representative point area or by the maximum r value, the minimum r value, the maximum θ value, and the minimum θ value of the distribution representative point area of the polar coordinate values.

Further, in the determination step, it may be determined whether an area of the distribution representative point area is equal to or greater than a predetermined distribution representative point area threshold value, and when determining that the area of the distribution representative point area is less than the distribution representative point area threshold value, it may be determined that the data group to be determined is not the relevant data group.

Further, in the determination step, it may be further determined whether an area of the overlapping area is equal to or greater than a predetermined overlapping area point area threshold value, and when determining that the area of the overlapping area is equal to or greater than the overlapping area threshold value, it may be determined that the data group to be determined is the relevant data group.

Further, in the determination step, it may be further determined whether a ratio of an area of the overlapping area to an area of the determination area is equal to or greater than a predetermined first ratio threshold value, and when determining that the ratio of the area of the overlapping area to the area of the determination area is equal to or greater than the predetermined first ratio threshold value, it may be determined that the data group to be determined is the relevant data group.

Further, in the determination step, it may be further determined whether a ratio of an area of the overlapping area to an area of the distribution representative point area is equal to or greater than a predetermined second ratio threshold value, and when determining that the ratio of the area of the overlapping area to the area of the distribution representative point area is equal to or greater than the predetermined second ratio threshold value, it may be determined that the data group to be determined is the relevant data group.

Further, any combination of the process using the predetermined distribution representative point area threshold value, the process using the predetermined overlapping area point area threshold value, the process using the predetermined first ratio threshold value, and the process using the predetermined second ratio threshold value may be performed. Namely, for example, some of the processes may be performed, or all of the processes may be performed.

Further, in the determination step, the distribution representative point area may be defined by sequentially connecting the representative points with lines in a manner such that the lines are not crossed over each other.

Further, in the distribution representative point selection step, the dividing straight line or the plural dividing straight lines provided may extend in a direction parallel to a direction of one axis of the coordinate axes of the coordinate plane, and in each of the divided areas, the data points having a maximum coordinate value and a minimum coordinate value along the other axis of the coordinate axes of the coordinate plane may be selected as the representative points of the divided area.

Further, in the distribution representative point selection step, in each of the divided areas, from among the data points in the divided area, an outermost data point in each of two directions may be selected as representative point candidate of the data point distribution area, each of the two directions being parallel to an extending direction of the dividing straight line or plural dividing straight lines, one second dividing straight line or plural second dividing straight lines parallel to each other may be provided, each of the second dividing straight lines crossing the dividing straight line and the data point distribution area, so that an area of the coordinate plane is divided into two or more divided areas, and a data point that is the outermost data point in each of the two directions being parallel to the extending direction of the second dividing straight line or the plural second dividing straight lines and that is the representative point candidate may be selected as the representative point.

Herein, the dividing straight lines and the second dividing straight lines may be orthogonal to each other. However, the dividing straight lines and the second dividing straight lines may not be orthogonal to each other.

Further the dividing straight lines may be parallel to the direction of one coordinate axis of the coordinate plane, and the second dividing straight lines may be parallel to the direction of the other coordinate axis of the coordinate plane.

Further, in the distribution representative point selection step, an area of the coordinate plane may be divided by the dividing straight lines and a third dividing straight line that crosses each of the dividing straight lines and that crosses the data point distribution area, and in each of the divided areas, the outermost data point from the third dividing straight line may be selected as the representative point.

Herein, the angle between the dividing straight lines and the third dividing straight line is not limited to a specific degrees. However, it is preferable that the angle be close to 90 degrees, and more preferably, the dividing straight lines and the third dividing straight line be orthogonal to each other.

Further, in the distribution representative point selection step, when there is no data point in a first divided area and there are two or more data points in a second divided area opposite to the first divided area across the third dividing straight line, from among the two or more data points in the second divided area, the data point closest to the third dividing straight line may be selected as the representative point of the first divided area.

Further, the third dividing straight line may be a regression line of the data points.

Further, in the distribution representative point selection step, from among the data points in the data point distribution area, the data points having a maximum coordinate value and a minimum coordinate value in one of two coordinate axes of the coordinate plane may be selected, and points that are on a regression line of the data points and that have the maximum coordinate value and the minimum coordinate value of the selected representative points may be selected as additional representative points.

According an embodiment of the present invention, there is provided a non-transitory computer-readable recording medium including a program encoded and stored in a computer readable format to cause a computer to execute the steps described above.

In an identification method according to an embodiment of the present invention, an area on the coordinate plane is divided into two or more divided areas by providing and using one dividing straight line or plural dividing straight lines parallel to each other, plural data points are expressed as data points on the coordinate plane, the plural data points constituting a data group to be determined, each of the plural data points including two variables as a pair, the dividing straight line or the plural dividing straight lines crossing a data point distribution area, the data point distribution area being a distribution are of the data points, and in each of the divided areas, from among the data points in the divided area, an outermost data point in each of two directions is selected as representative points of the data point distribution area, the two directions being parallel to an extending direction of the dividing straight line or plural dividing straight lines (distribution representative point selection step). Further, it is determined whether there is an overlapping area where a distribution representative point area overlaps a determination area, the distribution representative point area being defined by connecting the representative points with lines, the determination area being a specific area set on the coordinate plane, and when determining that there is the overlapping area, it is determined that the data group to be determined is a relevant data group (determination step).

By doing in this way, it may become possible to determine whether the data point distribution area of the data group to be determined is distributed in a specific determination area while the data point distribution area has been replaced by the distribution representative point area, in other words while the information amount expressing the data point distribution area has been decreased.

Further, in an identification method according an embodiment of the present invention, the data group to be determined may be any one of pattern defect inspection result data, particle inspection result data, and wafer test result data in a semiconductor device manufacturing process.

By doing this, it may become possible to extract a lot having wafers having similar pattern defect distribution status, particle (contamination, foreign matter) defect distribution status, or defect chip distribution status, so as to estimate the cause of defects caused by manufacturing apparatuses and manufacturing processes.

Further, in the identification method according an embodiment of the present invention, the information of the acquired representative points may be associated with information to be used to identify the data group to be determined and registered into a database (representative point information registration step). In this case, the representative point information registration step is performed before the determination step is performed, and in the determination step, it is determined whether there is the overlapping area by reading the information of the representative points associated with the information to be used to identify the data group to be determined from the database.

By doing in this way, it may not be necessary to perform the process of the distribution representative point selection step every time to perform the process of the determination step for the data group to be determined such as the pattern defect inspection result data, the particle inspection result data, and the wafer test result data, thereby enabling reducing the processing time.

Further, in the representative point information registration step, characteristic information may be associated with the information to be used to identifying the data group to be determined and stored in the database, the characteristic information including a distribution range of the data point distribution area, a distribution range of the distribution representative point area, and at least one of an area, a roundness rate, and a data point distribution density of the distribution representative point area, and in the determination step, after making a short list of the data groups to be determined based on the characteristic information, it may be determined whether there is the overlapping area.

By doing in this way, it may become possible to reduce the number of the data groups to be determined, thereby enabling reducing the processing time.

Further, in an identifying method according to an embodiment of the present invention, in the determination step, it may be determined whether an area of the distribution representative point area is equal to or greater than a predetermined distribution representative point area threshold value, and when determining that the area of the distribution representative point area is less than the distribution representative point area threshold value, it may be determined that the data group to be determined is not the relevant data group.

By doing in this way, when it is not desirable that the data group to be determined having a smaller distribution representative point area or a smaller data point distribution area be determined as a relevant data group, it may become possible to remove such a data group to be determined.

Further, when this process using the distribution representative point area threshold value is performed before it is determined whether there is the overlapping area, it may not be necessary to perform the process determining whether there is the overlapping area on the data group to be determined having a smaller distribution representative point area or a smaller data point distribution area.

Further, in the determination step, it may be further determined whether an area of the overlapping area is equal to or greater than a predetermined overlapping area point area threshold value, and when determining that the area of the overlapping area is equal to or greater than the overlapping area threshold value, it may be determined that the data group to be determined is the relevant data group.

By dong in this way, when it is not desirable that the data group to be determined having a smaller overlapping area is determined as a relevant data group, it may become possible to remove such a data group to be determined.

Further, in the determination step, it may be further determined whether a ratio of an area of the overlapping area to an area of the determination area is equal to or greater than a predetermined first ratio threshold value, and when determining that the ratio of the area of the overlapping area to the area of the determination area is equal to or greater than the predetermined first ratio threshold value, it may be determined that the data group to be determined is the relevant data group.

By dong in this way, when it is not desirable that the data group to be determined having a smaller ratio of the area of the overlapping area to the area of the determination area is determined as a relevant data group, it may become possible to remove such a data group to be determined.

Further, in the determination step, it may be further determined whether a ratio of an area of the overlapping area to an area of the distribution representative point area is equal to or greater than a predetermined second ratio threshold value, and when determining that the ratio of the area of the overlapping area to the area of the distribution representative point area is equal to or greater than the predetermined second ratio threshold value, it may be determined that the data group to be determined is the relevant data group.

By dong in this way, when it is not desirable that the data group to be determined having a smaller ratio of the area of the overlapping area to the area of the distribution representative point area is determined as a relevant data group, it may become possible to remove such a data group to be determined.

Further, in the determination step, the distribution representative point area may be defined by sequentially connecting the representative points with lines in a manner such that the lines are not crossed over each other.

By doing in this way, it may become possible to define the distribution representative point area in accordance with the contour of the data point distribution area.

Further, in the distribution representative point selection step, the dividing straight line or the plural dividing straight lines provided may extend in a direction parallel to a direction of one axis of the coordinate axes of the coordinate plane, and in each of the divided areas, the data points having a maximum coordinate value and a minimum coordinate value along the other axis of the coordinate axes of the coordinate plane may be selected as the representative points of the divided area.

By doing in this way, it may become possible to easily determine which of the divided areas include the data point based on the coordinate value of the data points in one axis of the coordinate axes. Further, it may become possible to select the representative point with a simple process by comparing the coordinate values of the data points in the other axis of the coordinate axes.

Further, in the distribution representative point selection step, in each of the divided areas, from among the data points in the divided area, an outermost data point in each of two directions may be selected as representative point candidates of the data point distribution area, each of the two directions being parallel to an extending direction of the dividing straight line or plural dividing straight lines, one second dividing straight line or plural second dividing straight lines parallel to each other may be provided, each of the second dividing straight lines crossing the dividing straight line and the data point distribution area, so that an area of the coordinate plane is divided into two or more divided areas, and a data point that is the outermost data point in each of the two directions being parallel to the extending direction of the second dividing straight line or the plural second dividing straight lines and that is the representative point candidate may be selected as the representative point.

By doing in this way, it may become possible to define the distribution area of the data point more appropriately.

In this case, when the dividing straight lines and the second dividing straight lines are orthogonal to each other, it may become possible to define the distribution area of the data point more appropriately.

Further, when the dividing straight lines are parallel to the direction of one coordinate axis of the coordinate plane and the second dividing straight lines are parallel to the direction of the other coordinate axis of the coordinate plane, it may be easier to determine which of the divided areas includes the data points based on the coordinate values of the data points, and by comparing the coordinate values of the data points, it may become possible to select the representative point candidate and the representative point with an easier process.

Further, in the distribution representative point selection step, an area of the coordinate plane may be divided by the dividing straight lines and a third dividing straight line that crosses each of the dividing straight lines and that crosses the data point distribution area, and in each of the divided areas, the outermost data point from the third dividing straight line may be selected as the representative point.

By doing in this way, in each of the divided areas, based on the distance between each of the data points and the third dividing straight line, it may become possible to select the data points disposed at an outermost position in each of the two directions parallel to the extending direction of the dividing straight line as the representative points.

Further, in the distribution representative point selection step, when there is no data point in first divided area and there are two or more data points in second divided area opposite to the first divided area across the third dividing straight line, from among the two or more data points in the second divided area, the data point closest to the third dividing straight line may be selected as the representative point of the first divided area.

By doing in this way, it may become possible to define the distribution area of the data points more appropriately.

In an identification method according to an embodiment of the present invention, in the distribution representative point selection step, depending on the settings of the dividing straight lines and the third dividing straight line, there may be a case where there are some divided areas including no data points. However, when the third dividing straight line is a regression line of the data points, it may become possible to reduce the number of the divided areas including no data points.

Further, in a case where the regression line is used as the third dividing straight line, when there is generated one or more divided areas including no data points, as described above, the data point in the opposite divided area across the regression line may be selected as the representative point of the divided area including no data points. However, it may become possible to define a more appropriate distribution representative point area when assuming that the divided area including no data points has no representative data.

Further, in an identification method according to an embodiment of the present invention, in the distribution representative point selection step, from among the data points in the data point distribution area, the data points having a maximum coordinate value and a minimum coordinate value in one of two coordinate axes of the coordinate plane may be selected, and points that are on a regression line of the data points and that have the maximum coordinate value and the minimum coordinate value of the selected representative points may be selected as additional representative points.

By doing in this way, it may become possible to define the distribution area of the data points more appropriately.

According to an embodiment of the present invention, there is provided a non-transitory computer-readable recording medium, including a program encoded and stored in a computer readable format to cause a computer to execute the steps described above. By using the recording medium, due to the program, it may become possible to cause a computer to execute the steps of the identification method according to an embodiment of the present invention.

Although the invention has been described with respect to specific embodiments for a complete and clear disclosure, the appended claims are not to be thus limited but are to be construed as embodying all modifications and alternative constructions that may occur to one skilled in the art that fairly fall within the basic teachings herein set forth.

For example, the figures are used for the description of the embodiments of the present invention. However, the figures may not be always necessary in any of the steps. Namely, with the information of the determination area and the data group of the plural data having two variables as a pair, each of the steps may be performed.

Further, in the above embodiments, an XY orthogonal coordinate plane is used. However, as a coordinate plane used in the present invention, the oblique coordinate plane may also be used.

The present invention may also be used for identifying whether the data group is distributed in a specific area, the data group including plural data having two variables as a pair.

What is claimed is:

1. An identification method performed by a computer to identify a data point distribution area on a coordinate plane, the identification method comprising:

a distribution representative point selection step of:
dividing an area on the coordinate plane into two or more divided areas by providing and using one dividing straight line or plural dividing straight lines parallel to each other, where plural data are expressed as data points on the coordinate plane, the plural data constituting a data group to be determined, each of the plural data including two variables as a pair, the dividing straight line or the plural dividing straight lines crossing the data point distribution area, the data point distribution area being a distribution area of the data points, and selecting, in each of the divided areas, from among the data points in the divided area, an outermost data point in each of two directions as representative points of the data point distribution area, the two directions being parallel to an extending direction of the dividing straight line or the plural dividing straight lines; and a determination step of:
determining whether there is an overlapping area where a distribution representative point area overlaps a determination area, the distribution representative point area being defined by connecting the representative points with lines, the determination area being a specific area set on the coordinate plane, and determining, when determining that there is the overlapping area, that the data group to be determined is a relevant data group.

2. The identification method according to claim 1, wherein the data group to be determined is any one of pattern defect inspection result data, particle inspection result data, and wafer test result data in a semiconductor device manufacturing process.

3. The identification method according to claim 1, further comprising:

a representative point information registration step of associating and registering information of the representative points acquired in the distribution representative point selection step with information to be used to identify the data group to be determined into a database, wherein the representative point information registration step is performed before the determination step is performed, and in the determination step, it is determined whether there is the overlapping area by reading the information of the representative points associated with the information to be used to identify the data group to be determined from the database.

4. The identification method according to claim 3, wherein in the representative point information registration step, characteristic information is associated with the information to be used to identify the data group to be determined and stored in the database, the characteristic information including a distribution range of the data point distribution area, a distribution range of the distribution representative point area, and at least one of an area, a roundness rate, and a data point distribution density of the distribution representative point area, and in the determination step, after making a short list of the data groups to be determined based on the characteristic information, it is determined whether there is the overlapping area.

5. The identification method according to claim 1, wherein in the determination step, it is determined whether an area of the distribution representative point area is equal to or greater than a predetermined distribution representative point area threshold value, and when determining that the area of the distribution representative point area is less than the distribution representative point area threshold value, it is determined that the data group to be determined is not the relevant data group.

6. The identification method according to claim 1, wherein
in the determination step, it is further determined whether an area of the overlapping area is equal to or greater than a predetermined overlapping area point area threshold value, and
when determining that the area of the overlapping area is equal to or greater than the overlapping area threshold value, it is determined that the data group to be determined is the relevant data group.

7. The identification method according to claim 1, wherein
in the determination step, it is further determined whether a ratio of an area of the overlapping area to an area of the determination area is equal to or greater than a predetermined first ratio threshold value, and
when determining that the ratio of the area of the overlapping area to the area of the determination area is equal to or greater than the predetermined first ratio threshold value, it is determined that the data group to be determined is the relevant data group.

8. The identification method according to claim 1, wherein
in the determination step, it is further determined whether a ratio of an area of the overlapping area to an area of the distribution representative point area is equal to or greater than a predetermined second ratio threshold value, and
when determining that the ratio of the area of the overlapping area to the area of the distribution representative point area is equal to or greater than the predetermined second ratio threshold value, it is determined that the data group to be determined is the relevant data group.

9. The identification method according to claim 1, wherein
in the determination step, the distribution representative point area is defined by sequentially connecting the representative points with lines in a manner such that the lines are not crossed over each other.

10. The identification method according to claim 1, wherein
in the distribution representative point selection step, the dividing straight line or the plural dividing straight lines provided extend in a direction parallel to a direction of one axis of the coordinate axes of the coordinate plane, and in each of the divided areas, the data points having a maximum coordinate value and a minimum coordinate value along the other axis of the coordinate axes of the coordinate plane are selected as the representative points of the divided area.

11. The identification method according to claim 1, wherein
in the distribution representative point selection step, in each of the divided areas, from among the data points in the divided area, an outermost data point in each of two directions is selected as representative point candidates of the data point distribution area, the two directions being parallel to an extending direction of the dividing straight line or plural dividing straight lines,
one second dividing straight line or plural second dividing straight lines parallel to each other are provided, each of the second dividing straight lines crossing the dividing straight line and the data point distribution area, so that an area of the coordinate plane is divided into two or more divided areas, and
data points that are the respective outermost data points in the two directions being parallel to the extending direction of the second dividing straight line or the plural second dividing straight lines and that are the representative point candidates are selected as the representative points.

12. The identification method according to claim 11, wherein
the dividing straight lines and the second dividing straight lines are orthogonal to each other.

13. The identification method according to claim 12, wherein
the dividing straight lines are parallel to the direction of one coordinate axis of the coordinate plane, and the second dividing straight lines are parallel to the direction of the other coordinate axis of the coordinate plane.

14. The identification method according to claim 1, wherein
in the distribution representative point selection step, an area of the coordinate plane is divided by the dividing straight lines and a third dividing straight line that crosses each of the dividing straight lines and that crosses the data point distribution area, and
in each of the divided areas, the outermost data point from the third dividing straight line is selected as the representative point.

15. The identification method according to claim 14, wherein
the dividing straight lines and the third dividing straight line are orthogonal to each other.

16. The identification method according to claim 14, wherein
in the distribution representative point selection step, when there is no data point in a first divided area and there are two or more data points in a second divided area opposite to the first divided area across the third dividing straight line, from among the two or more data points in the second divided area, the data point closest to the third dividing straight line is selected as the representative point of the first divided area.

17. The identification method according to claim 14, wherein
the third dividing straight line is a regression line of the data points.

18. The identification method according to claim 1, wherein
in the distribution representative point selection step, from among the data points in the data point distribution area, the data points having a maximum coordinate value and a minimum coordinate value in one of two coordinate axes of the coordinate plane are selected, and points that are on a regression line of the data points and that have the maximum coordinate value and the minimum coordinate value of the selected representative points are selected as additional representative points.

19. A non-transitory computer-readable recording medium, comprising a program encoded and stored in a computer readable format to cause a computer to execute an identification method for identifying a data point distribution area on a coordinate plane, the identification method comprising
a distribution representative point selection step of:
dividing an area on the coordinate plane into two or more divided areas by providing and using one dividing straight line or plural dividing straight lines parallel to each other, where plural data are expressed as data points on the coordinate plane, the plural data constituting a data group to be determined, each of the plural data including two variables as a pair, the dividing straight line or the plural dividing straight lines crossing the data point distribution area, the data point distribution area being a distribution area of the data points, and selecting, in each of the divided areas, from among the data points in the divided area, an outermost data point in each of two directions as representative points of the data point distribution area, the two directions being parallel to an extending direction of the dividing straight line or the plural dividing straight lines: and a determination step of:

determining whether there is an overlapping area where a distribution representative point area overlaps a determination area, the distribution representative point area being defined by connecting the representative points with lines, the determination area being a specific area set on the coordinate plane and determining when determining, that there is the overlapping area that the data group to be determined is a relevant data group.

* * * * *